(12) United States Patent
Ko

(10) Patent No.: US 11,135,229 B2
(45) Date of Patent: Oct. 5, 2021

(54) CAT AND DOG STERILIZATION BY ESTROGENIC COMPOUNDS

(71) Applicant: Insigna Inc., Champaign, IL (US)

(72) Inventor: CheMyong Ko, Champaign, IL (US)

(73) Assignee: Insigna Inc., Champaign, IL (US)

( * ) Notice: Subject to any disclaimer, the term of this patent is extended or adjusted under 35 U.S.C. 154(b) by 0 days.

(21) Appl. No.: 16/526,874

(22) Filed: Jul. 30, 2019

(65) Prior Publication Data

US 2020/0171047 A1 Jun. 4, 2020

Related U.S. Application Data

(60) Provisional application No. 62/772,878, filed on Nov. 29, 2018.

(51) Int. Cl.
*A61K 31/565* (2006.01)
*A61K 9/00* (2006.01)
*A61K 9/48* (2006.01)

(52) U.S. Cl.
CPC .......... *A61K 31/565* (2013.01); *A61K 9/0024* (2013.01); *A61K 9/48* (2013.01)

(58) Field of Classification Search
CPC ....... A61K 31/565; A61K 9/0024; A61K 9/48
See application file for complete search history.

(56) References Cited

U.S. PATENT DOCUMENTS

| | | | |
|---|---|---|---|
| 3,991,750 A | 11/1976 | Vickery | |
| 4,123,519 A * | 10/1978 | Tribble | A61K 39/0006 424/194.1 |
| 5,035,891 A | 7/1991 | Runkel et al. | |
| 5,314,882 A * | 5/1994 | Pantic | A61K 31/565 514/170 |
| 6,458,387 B1 * | 10/2002 | Scott | A61K 9/1635 424/484 |
| 7,589,082 B2 * | 9/2009 | Savoir | A61K 9/0019 514/170 |

OTHER PUBLICATIONS

Hayashi, Sterilization of Female Rats by Neonatal Placement of Estradiol Micropellets in Anterior Hypothalamus, 1976, Endocrinol. Japan., vol. 23 iss. 1, pp. 55-60. (Year: 1976).*
Rose-E-Silva et al., Prepubertal Administration of Estradiol Valerate Disrupts Cyclicity and Leads to Cystic Ovarian Morphology during Adult Life in the Rat: Role of Sympathetic Innervation, 2003, Endocrinology, vol. 144 iss. 19, pp. 4289-4297. (Year: 2003).*
"U.S. Appl. No. 16/699,307, Final Office Action dated Jan. 11, 2021", 12 pgs.
"U.S. Appl. No. 16/699,307, Response filed Nov. 12, 2020 to Non Final Office Action dated May 12, 2020", 8 pgs.
"International Application Serial No. PCT/US2019/044230, International Search Report dated Oct. 29, 2019", 2 pgs.
"International Application Serial No. PCT/US2019/044230, Written Opinion dated Oct. 29, 2019", 4 pgs.
Gorski, R A, "Modification of ovulatory mechanisms by postnatal administration of estrogen to the rat", American Journal of Physiology, vol. 205, No. 5, (1963), 842-844.
"International Application Serial No. PCT/US2019/044230, International Preliminary Report on Patentability dated Jun. 10, 2021", 6 pgs.
"U.S. Appl. No. 16/699,307, Non Final Office Action dated Jun. 28, 2021", 16 pgs.

* cited by examiner

*Primary Examiner* — Ali Soroush
(74) *Attorney, Agent, or Firm* — Schwegman Lundberg & Woessner, P.A.

(57) ABSTRACT

Methods, compositions and systems are presented to deliver estradiol benzoate to an animal so as to sterilize the animal. A physiologically acceptable oil or other carrier in a capsule is used to deliver the estradiol benzoate. The estradiol benzoate is delivered intraperitoneally, intramuscularly, or subcutaneously to a companion or livestock animal.

12 Claims, 40 Drawing Sheets

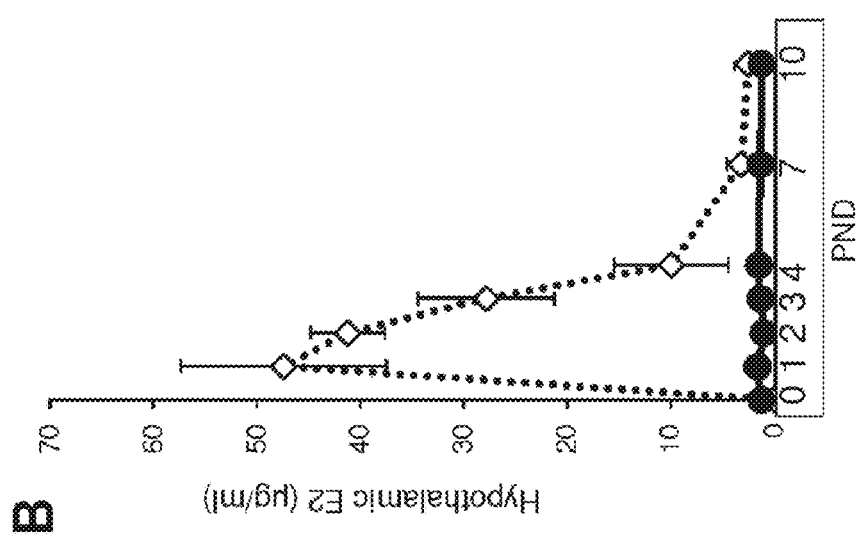
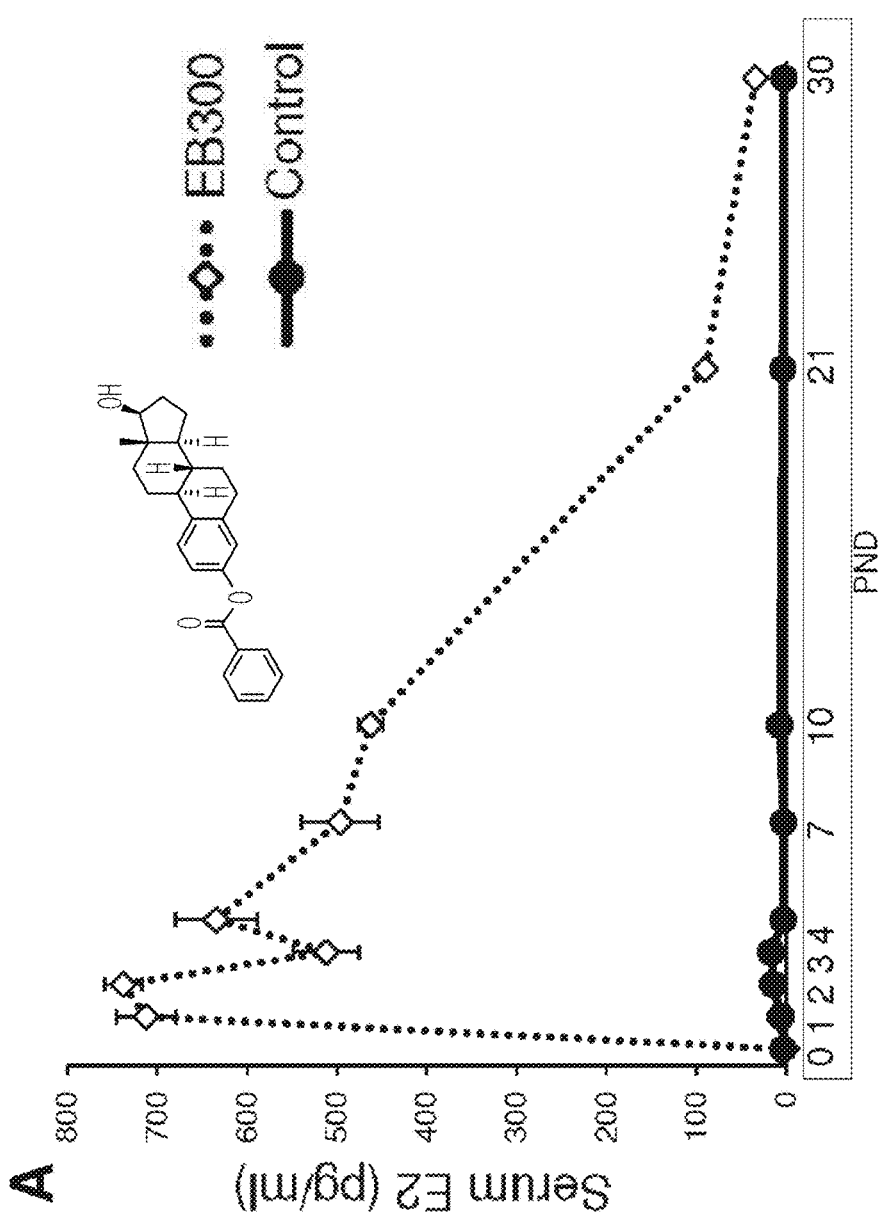
FIGs. 1A-B

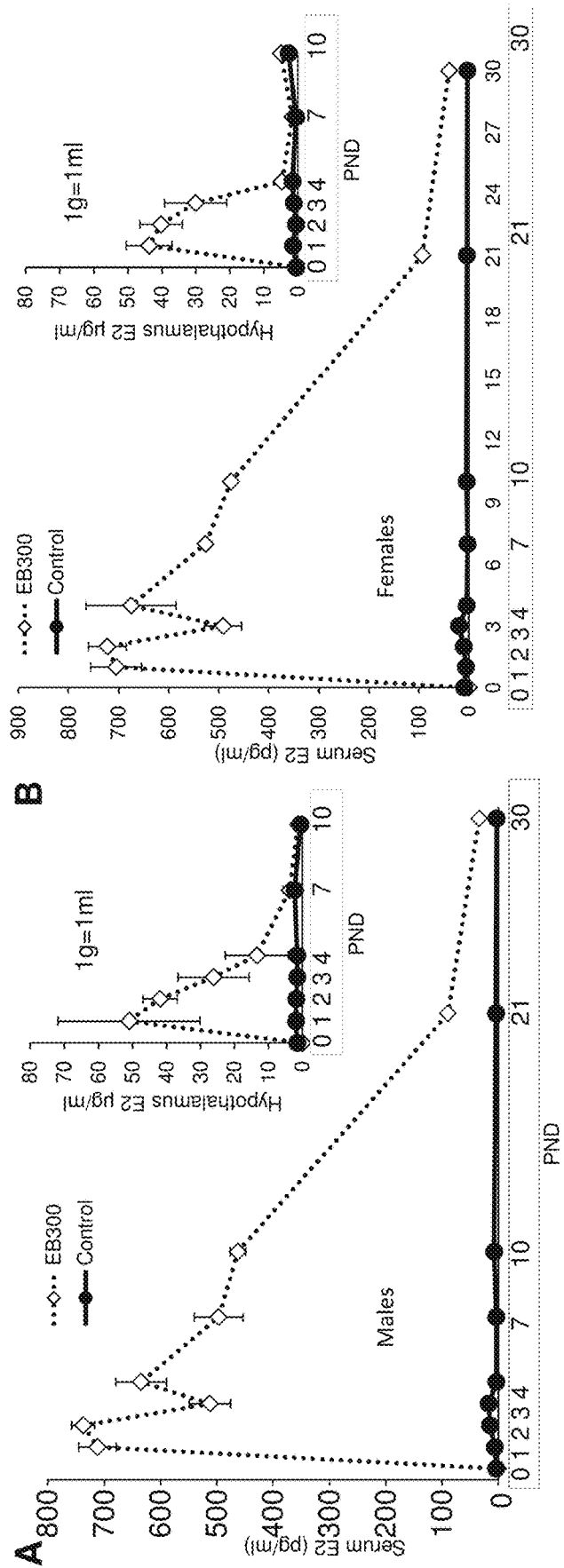
FIGs. 2A-B

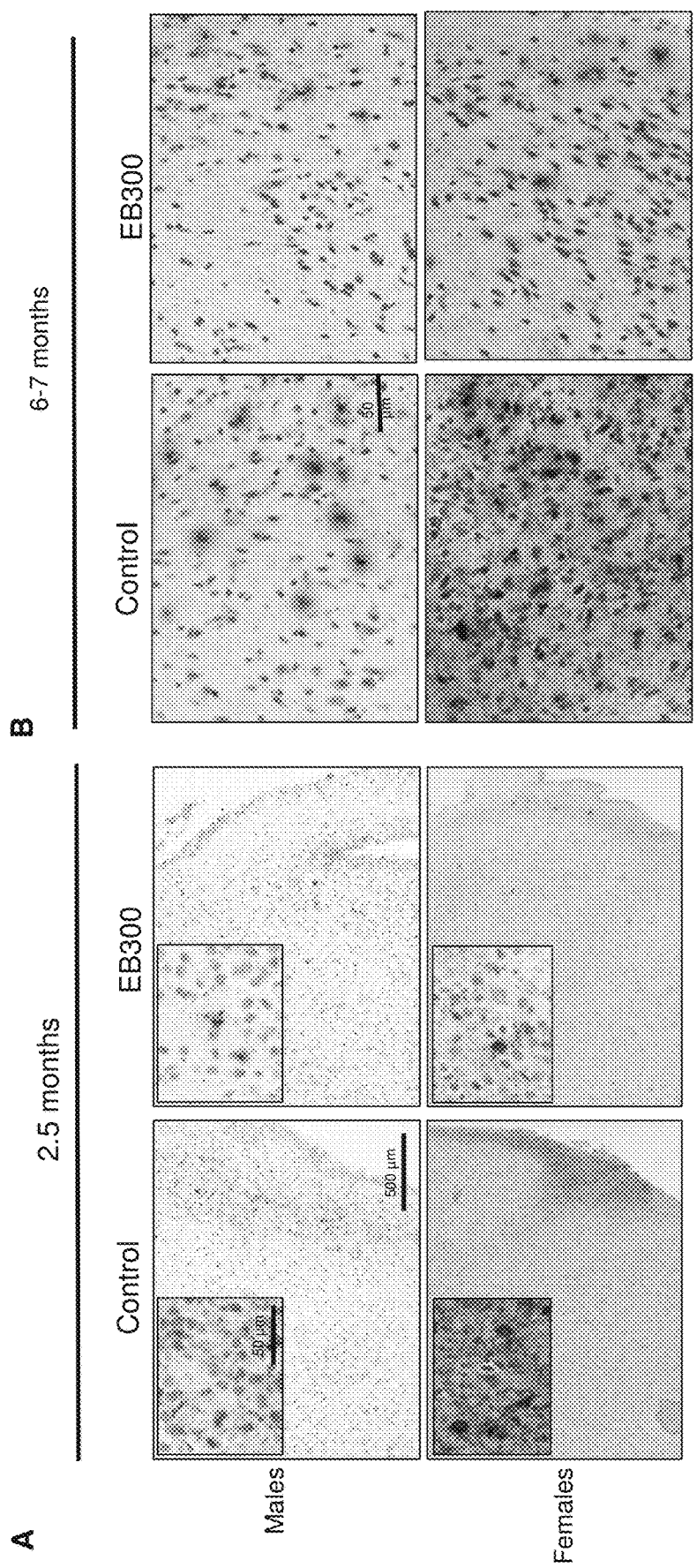
FIGs. 3A-B

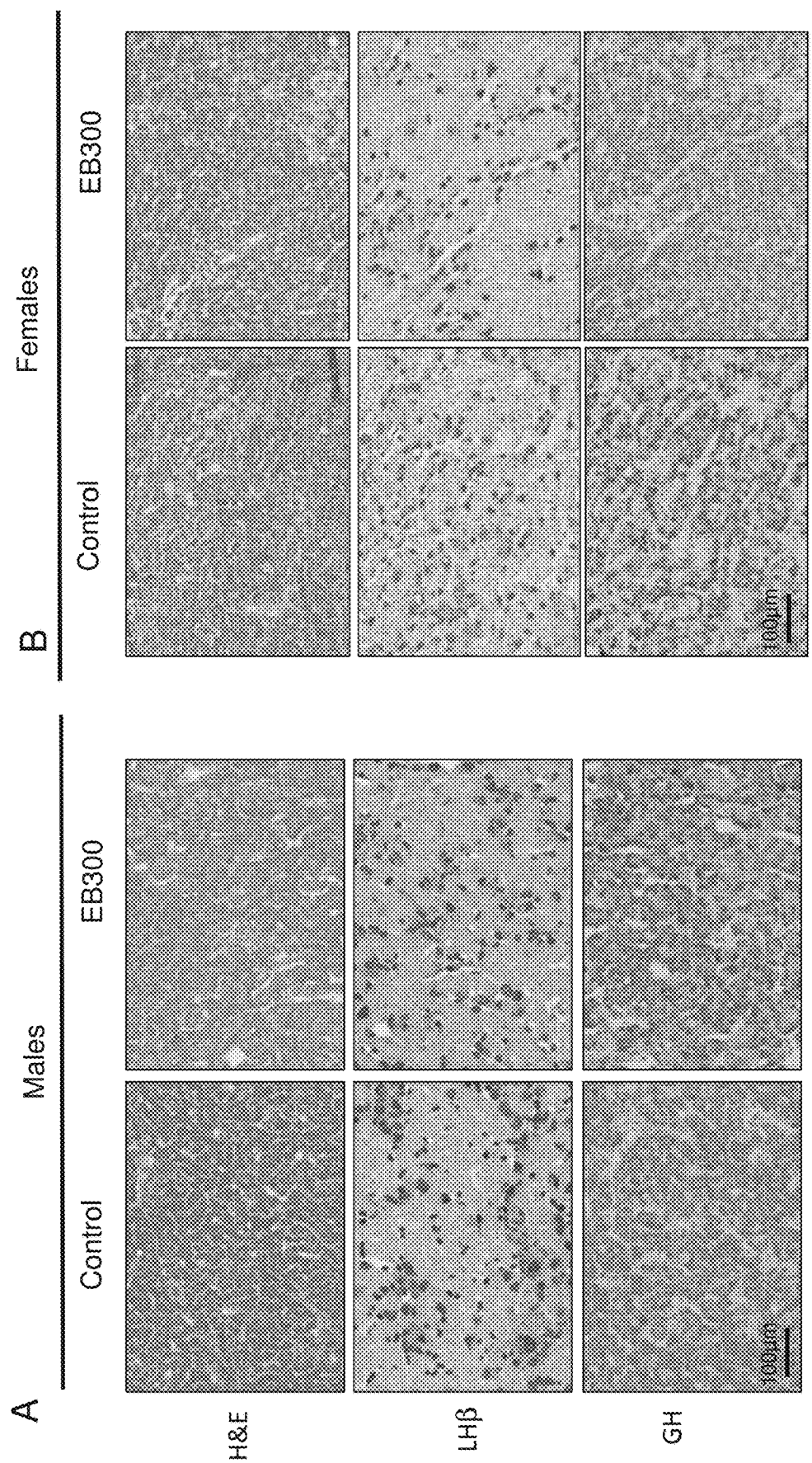
FIGs. 5A-B

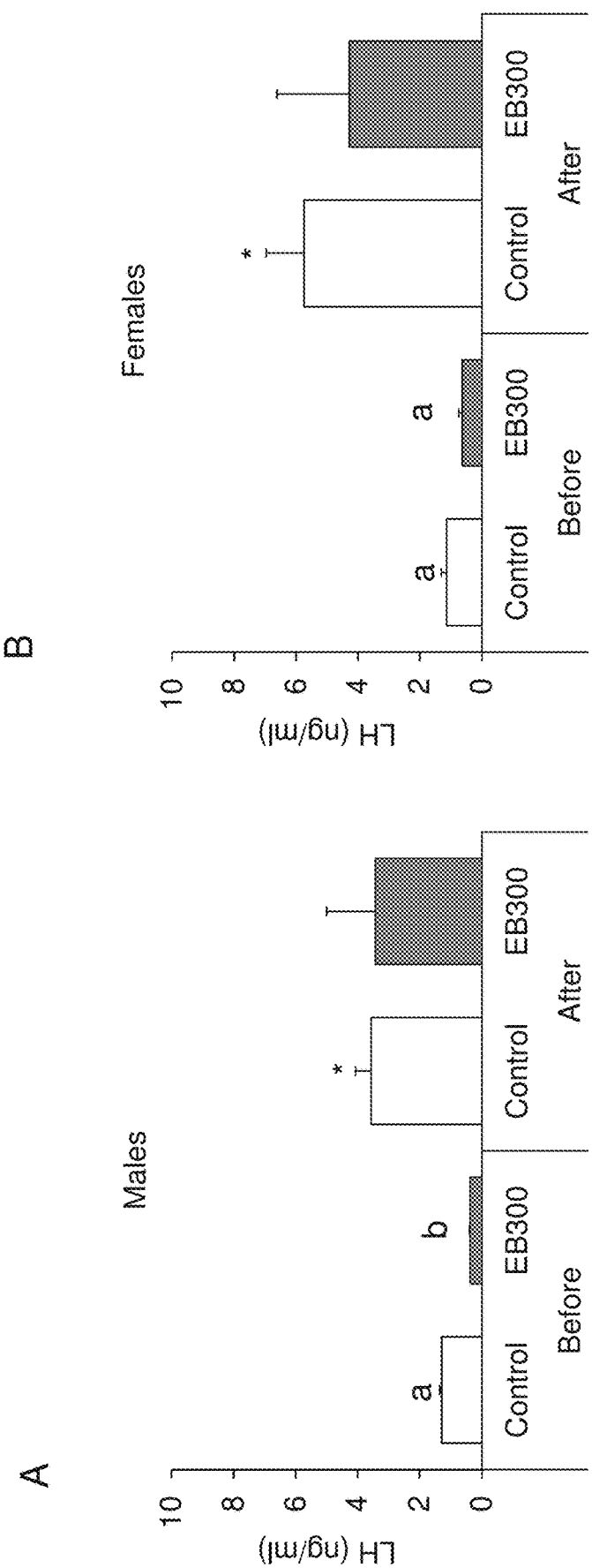
FIGs. 6A-B

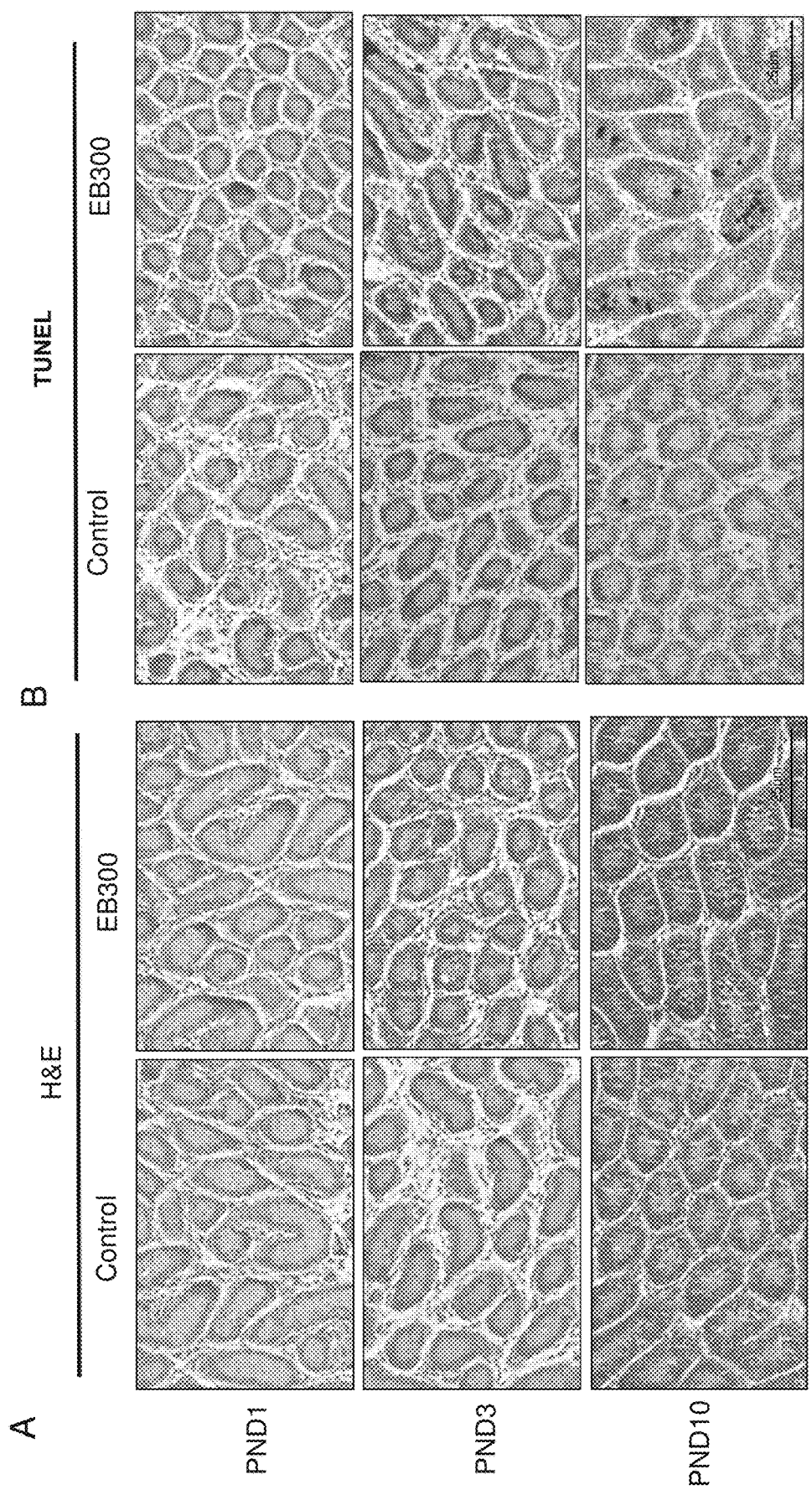
FIGs. 7A-B

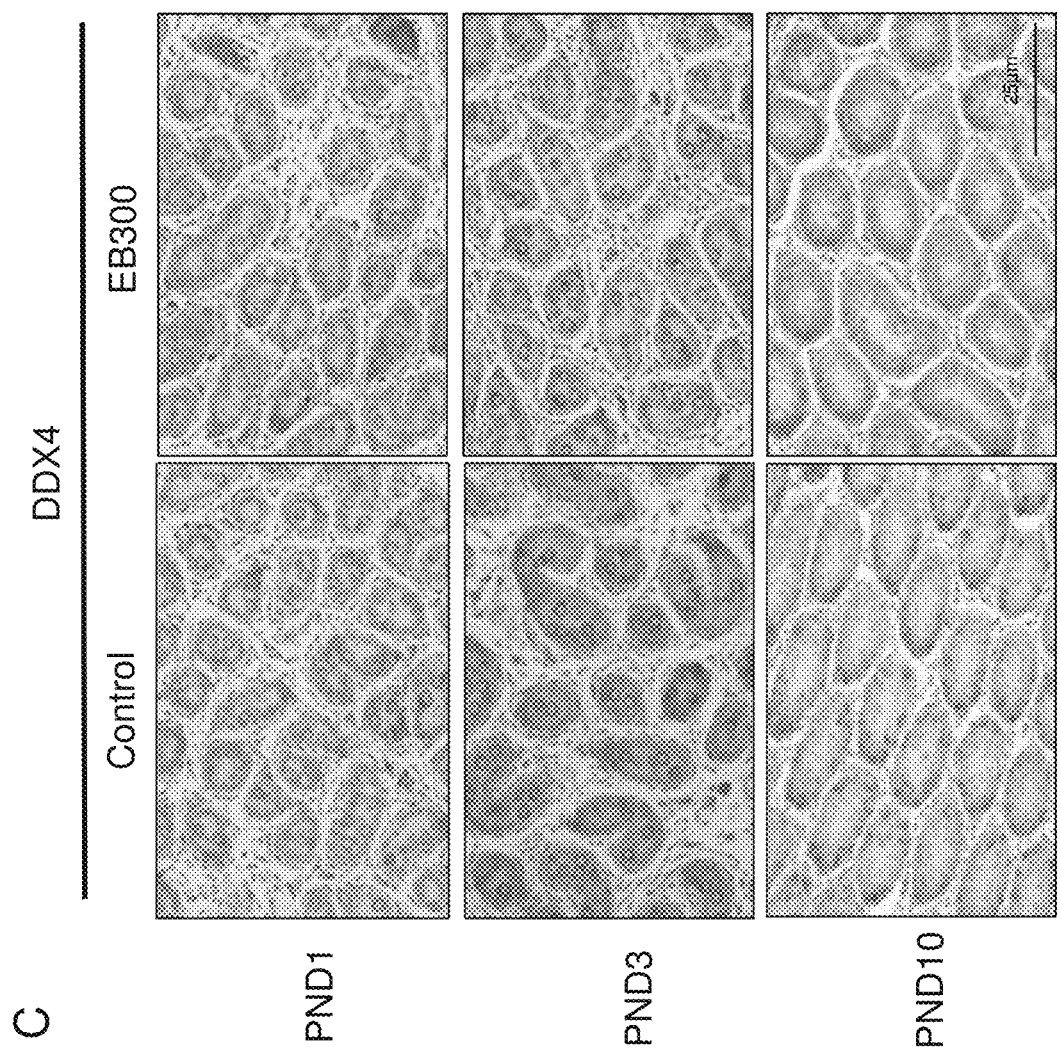

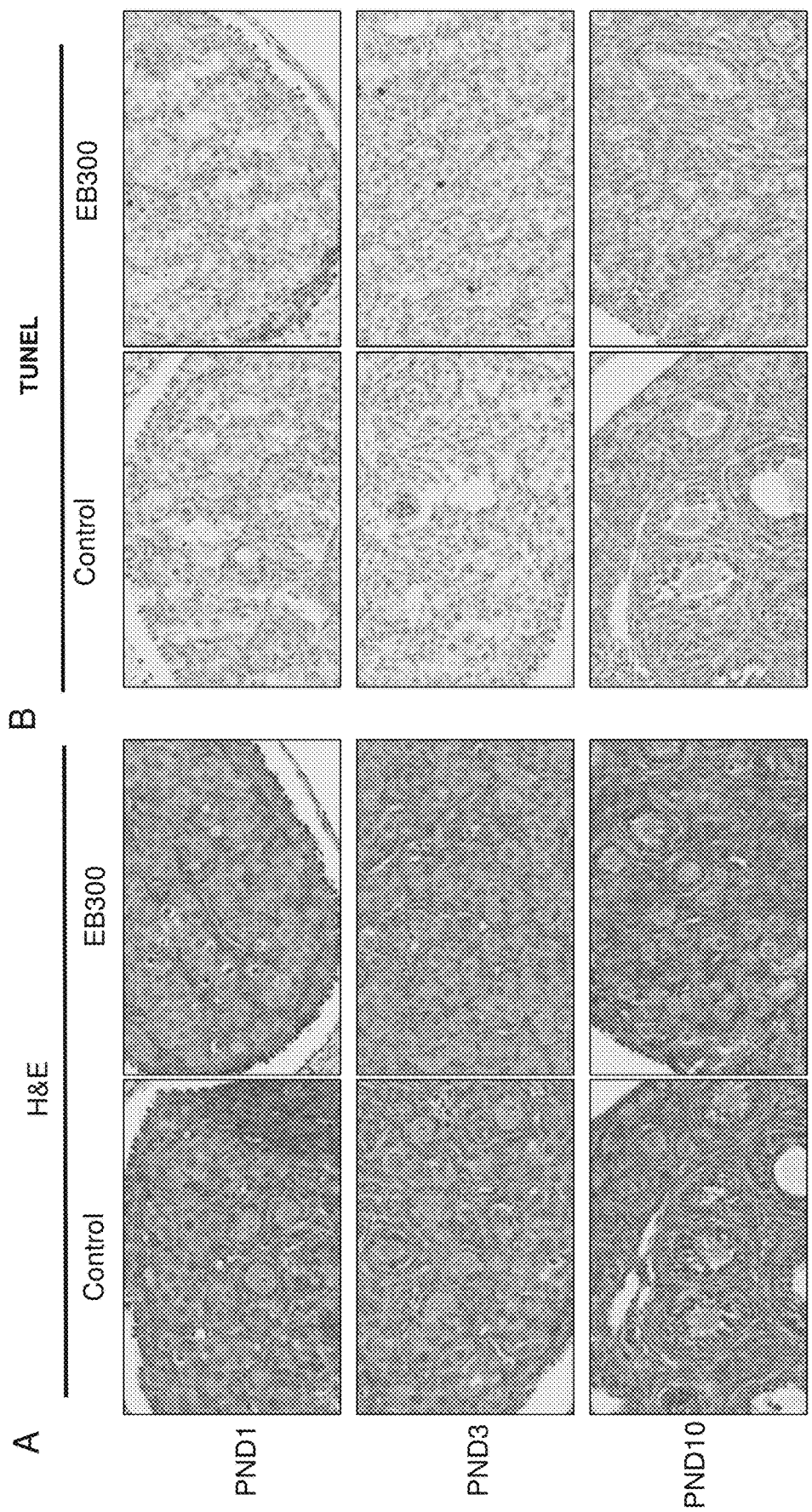
FIGs. 8A-B

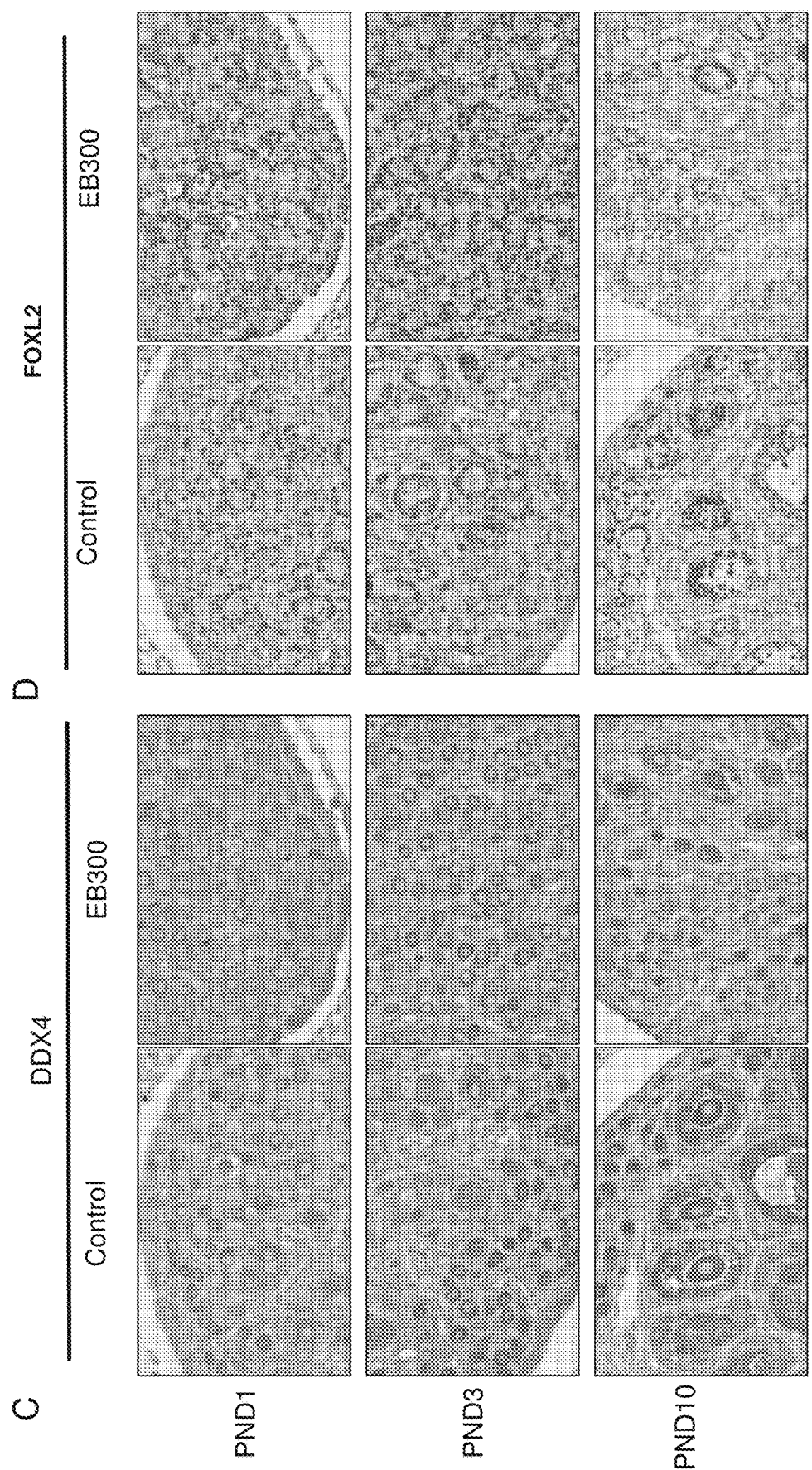
FIGs. 8C-D

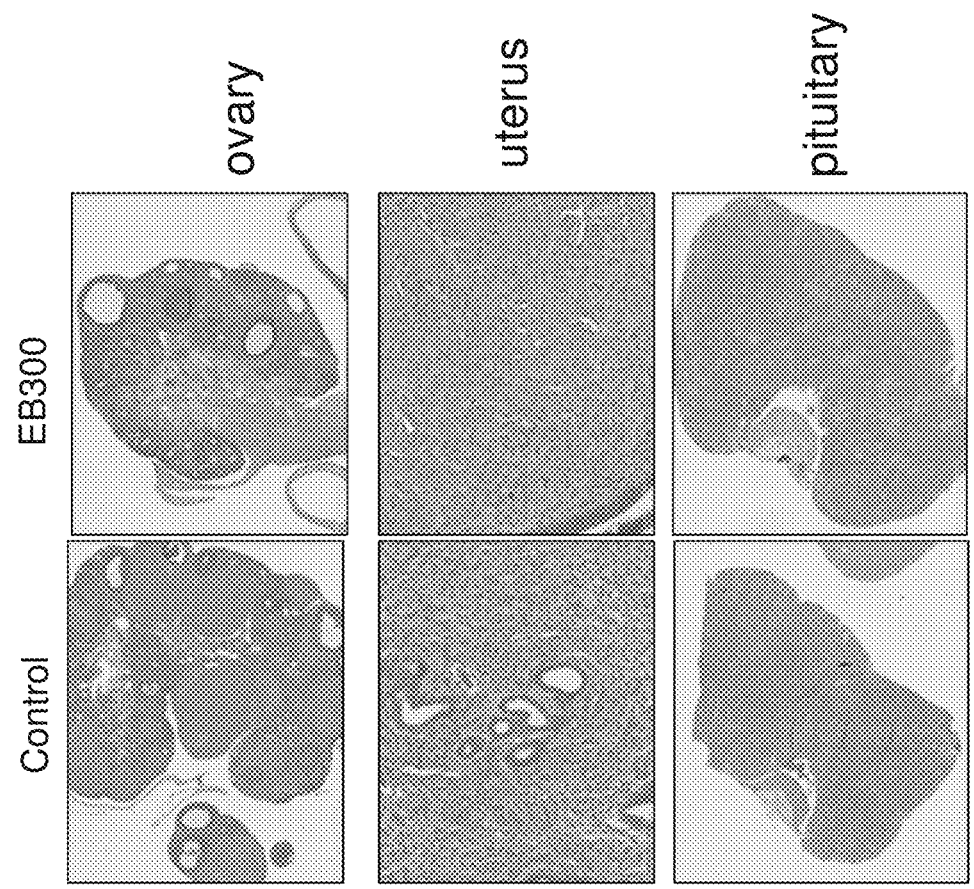
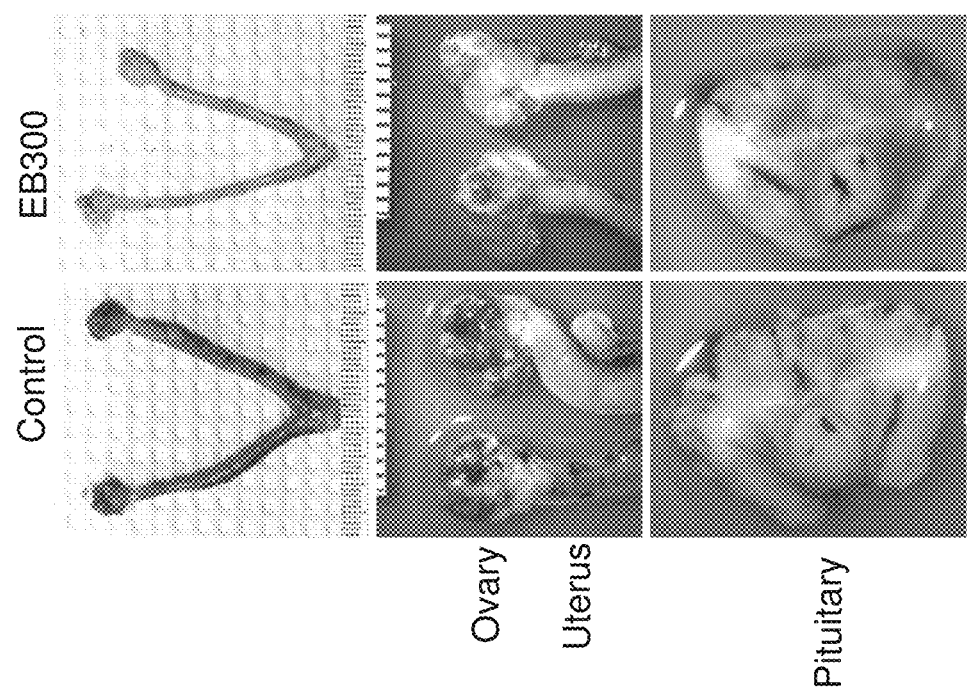
FIG. 9

FIGs. 19A-B

CAT AND DOG STERILIZATION BY ESTROGENIC COMPOUNDS

CROSS-REFERENCE TO RELATED APPLICATIONS

This application claims priority under 35 U.S.C. § 119(e) to U.S. Provisional Application No. 62/772,878, filed on Nov. 29, 2018, the disclosure of which is incorporated herein by reference in its entirety.

BACKGROUND

Sterilization, also referred to as neutering/spaying (or inducing infertility), refers to rendering an animal (male or female) incapable of reproduction. Sterilization involves either partial or complete removal of the reproductive organs or rendering the reproductive organs nonfunctional. Sterilization has assumed an important role for companion and food animals over time for various purposes. In companion animals such as dogs and cats, animals are sterilized mainly to control population, mitigating pet overpopulation and subsequent costs associated with caring for these animals.

In food animals such as bovines and swine, sterilization is primarily performed on males by castration as a means of decreasing testosterone production. The presence of testosterone in a food animal causes unpleasant, pungent odors when its meat is processed and cooked, particularly in meat from swine. Castration can also result in a higher grade of meat, i.e., meat that is leaner and has a higher content of intramuscular fat, also known as marbling, particularly in bovine meat. Furthermore, castration reduces aggression, particularly by the male animals, reducing potential physical hazards to other livestock or to human handlers.

Currently, sterilization of both companion and food animals is achieved primarily by surgical methods: physical removal of testes in males and removal of ovaries and uteri in females. However, multiple issues exist with the use of surgical sterilization methods. For example, surgical sterilization can be painful for the animal, expensive for the animal's owner, and can lead to secondary complications such as infection. Such complications can lead to additional treatment costs and an increased risk of further injury to, or death of, the animal.

In some male food animals such as bulls, castration is achieved by non-surgical methods, such as the use of an elastomeric ring to block or otherwise damage the blood supply to the testicles, leading to the death of testicular tissue. Typically, both surgical and non-surgical castration of livestock are performed without anesthesia or other pain management, which inevitably causes great discomfort/pain in the animals.

For these reasons, there is a need for a non-invasive, humane method for sterilizing animals.

SUMMARY

The use of estradiol benzoate (EB) as a novel method of sterilizing an animal is described herein.

One embodiment provides a method for inducing infertility in an animal by administering to said animal an effective amount of estradiol benzoate (EB) so as to render the animal infertile/sterile permanently. In one embodiment, the EB is administered with a carrier, such as an oil. In another embodiment, the EB is formulated as a slow release formulation. In one embodiment, the administration is a single, one time, dose. In some embodiments, the compositions can be administered intraperitoneally, intramuscularly, or subcutaneously. In one embodiment, the animal is a companion animal. In another embodiment, the animal is a livestock animal. In one embodiment, the EB is administered prior to puberty. Also provided herein is the use of EB to induce sterility.

Another embodiment provides a system to deliver a sterilant to an animal, the system comprising: a capsule comprising estradiol benzoate, and a device to deliver the capsule to the animal. In one embodiment, the capsule is formulated to release the EB for a pre-determined period. In one embodiment, the delivery device is an injector comprising a main body and a force member. In another embodiment, the EB is administered intraperitoneally, intramuscularly, or subcutaneously. In one embodiment, the animal is a companion animal. In another embodiment, the animal is a livestock animal.

This summary is intended to provide an overview of the subject matter of the present disclosure. It is not intended to provide an exclusive or exhaustive explanation of the invention. The detailed description is included to provide further information about the present disclosure.

ABBREVIATIONS

EB Estradiol benzoate
E2 Estradiol
AVPV Anteroventral Periventricular nucleus
ARC Arcuate nucleus
POA Preoptic area
KISS1 Kisspeptin protein
Kiss1 Kisspeptin gene or mRNA.
LHβ Luteinizing Hormone subunit beta
GH Growth Hormone
CASA Computer assisted semen analysis

BRIEF DESCRIPTION OF THE DRAWINGS

The drawings illustrate generally, by way of example but not by way of limitation, various embodiments discussed in the present document. In the drawings, which are not necessarily drawn to scale, like numerals may describe similar components in different views. Like numerals having different letter suffixes may represent different instances of similar components.

FIGS. 1A-B depict serum and hypothalamic E2 levels after implanting EB300 in rat pups on the day of birth (EB300 is a silastic capsule containing 300 micrograms of EB; implantation is defined herein as method of placing a capsule subcutaneously in an animal). EB300 was implanted on the day of birth, and the E2 concentrations were measured in the sera on postnatal day 0 (PND 0) to PND 30 (A) and the hypothalami on PND 0 to PND 10. The serum E2 levels are maintained at high levels until PND 10 and significantly decreased by PND 21, whereas hypothalamic E2 level was decreased to the basal level by PND 10. Also note the difference of E2 measurement units between serum (pg/ml) and hypothalamic (mg/ml). The numbers of animals used for each time point of serum and hypothalamic E2 measurements were 3-8 and 3-7 for each assay point, respectively. The data are from mixed numbers of males and females. FIG. 2 shows data from males and females separately.

FIGS. 2A-B depict serum and hypothalamic E2 levels after EB300 implantation. EB300 was implanted on the day of birth, and the E2 concentrations were measured in the sera on PND 0 to PND 30 (A) and the hypothalami on PND 0 to PND 10. The numbers of animals used for each time point of serum and hypothalamic E2 measurements were 3-8 and 3-7 for each point of the assays, respectively.

FIGS. 3A-B show KISS expression in the ARC of the hypothalamus. (A) Hypothalami of 2.5-month-old rats were stained by anti-KISS1 antibody. Shown are low and high magnification images taken from the ARC of the hypothalamus. (B) Hypothalami of rats 6-7 months of age were stained by anti-KISS1 antibody. Shown are high magnification images taken from the ARC. Note the lower KISS immunoreactivity in the EB300 hypothalmi.

FIGS. 5A-B depict histology and expression levels of LH and GH in the pituitaries. (A) Pituitaries of five- to six-month-old males were examined by histology (H&E staining) and immunohistochemistry for β-subunit of luteinizing hormone (LHβ) and growth hormone (GH). Shown are representative images of tissues from the Control and EB300 groups. (B) Pituitaries of five- to six-month-old males were examined by histology and immunohistochemistry for LHβ and GH. Shown are representative images of tissues from the Control and EB300 groups.

FIGS. 6A-B show serum LH concentrations before and after KISS-10 challenge. Serum levels of LH were measured 30 minutes after intraperitoneal injection of 50 nmole/animal KISS-1 at the ages 2-2.5 months. (A) Measurement in males. Number of animals used: Control group (n=6) and EB300 group (n=3). (B) Measurement in females. Number of animals used: Control group (n=4) and EB300 group (n=2). Asterisks indicate significant (p<0.05) differences from KISS-1 injections. "a" and "b" indicate significant (p<0.05) differences among all groups before KISS-1 injections.

FIGS. 7A-C depict neonatal gonadal development in males. Testes of PND 1, 3, and 10 were stained with H&E (A) or TUNEL (B), and DDX4 (Dead-box helicase-4) (C). Shown are representative images of testes from four animals per group.

FIGS. 8A-D depict neonatal gonadal development in females. Ovaries of PND 1, 3, and 10 were stained with H&E (A) or TUNEL (B), DDX4 (C) and FOXL2 (D). Shown are representative images of ovaries from four animals per group.

FIG. 9 depicts ovary, uterus, and pituitary at 5.5 months. Images were taken immediately after tissue collection or after H&E staining.

Serum estradiol concentrations were measured at the ages of two months and 6-7 months in males. Shown are mean±SEM; * indicates p<0.05 when compared with the control group. Serum estradiol concentrations were measured at two months and six months of age.

FIGS. 19A-B depict changes in body weight over time. Body weight was measured at PND 0, 6, 14, 21, 28, 42, 60, 90, 120, 150, and 180 in the males (A) and females (B). Data are mean±SEM. (n=3-7 for each time point).

Figure 20:
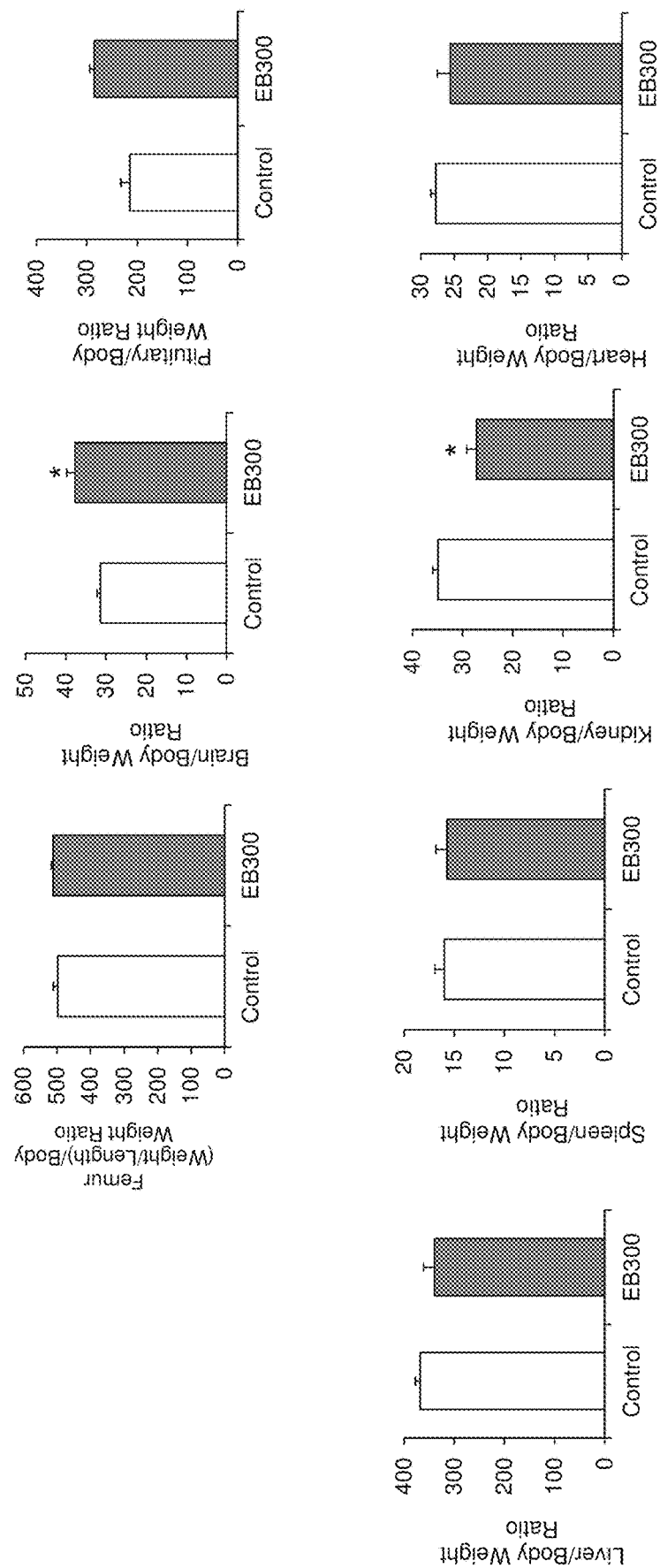

FIG. 20 shows organ weights in males. Femur bone (weight/length), brain (weight), pituitary (weight), liver (weight), spleen (weight), kidney (weight), and heart (weight) were each divided by body weight to investigate the impaired growth of essential organs. Error bars indicate SEM; * indicates a significant difference from the control (Student t-test, p<0.05). (6-7 months; n=7,8).

Figure 21:
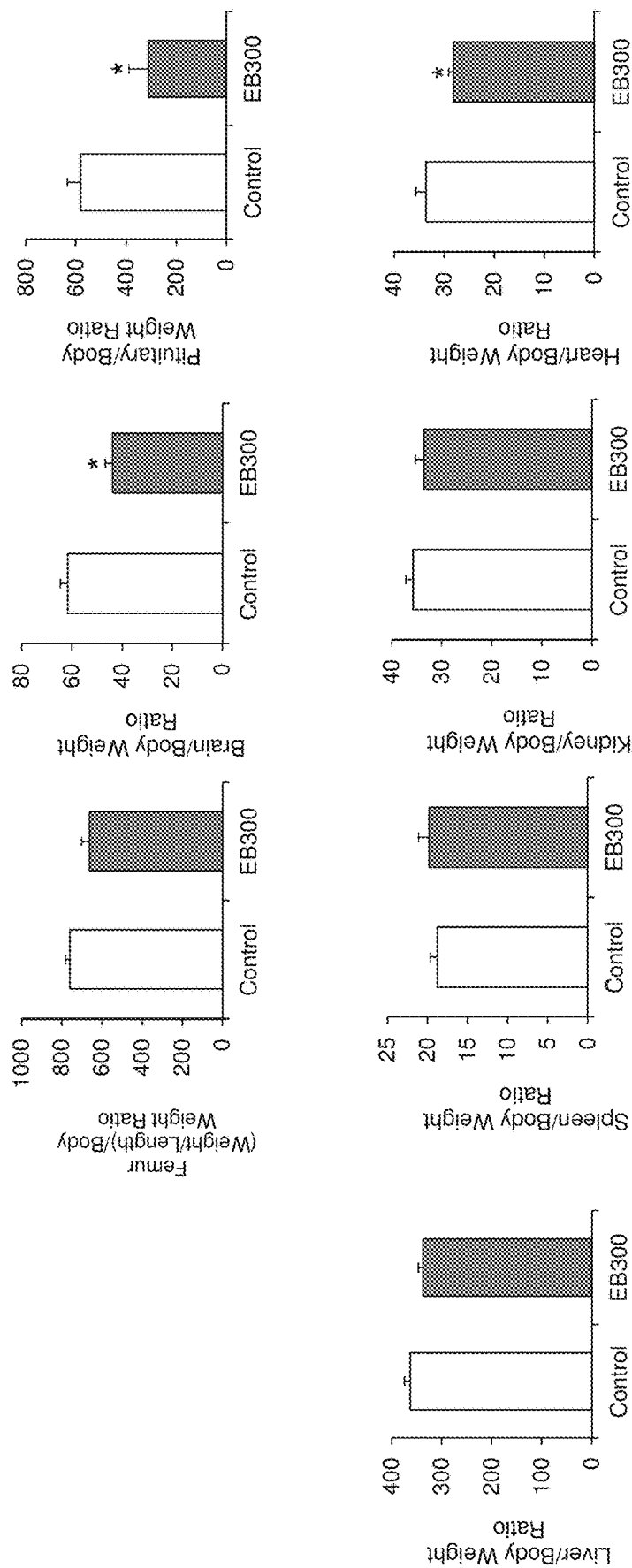

FIG. 21 shows organ weights in females. Femur bone (weight/length), brain (weight), pituitary (weight), liver (weight), spleen (weight), kidney (weight), and heart (weight) were each divided by body weight to investigate the impaired growth of essential organs. Error bars indicate SEM. * indicates a significant difference from control (Student t-test, p<0.05). (6-7 months; n=7,8).

Figure 22:
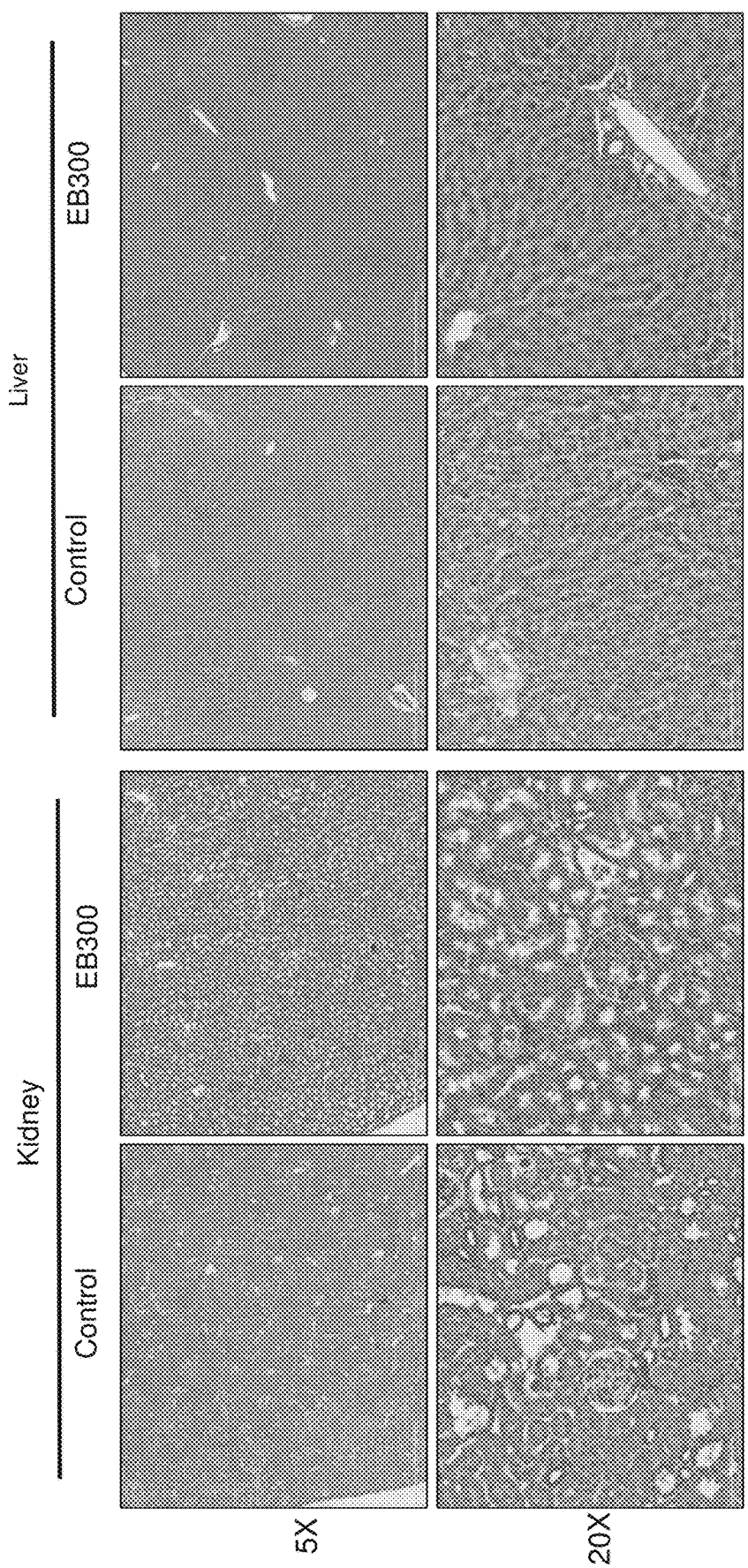

FIG. 22 shows representative kidney and liver histology in males (5-6 months).

Figure 23:
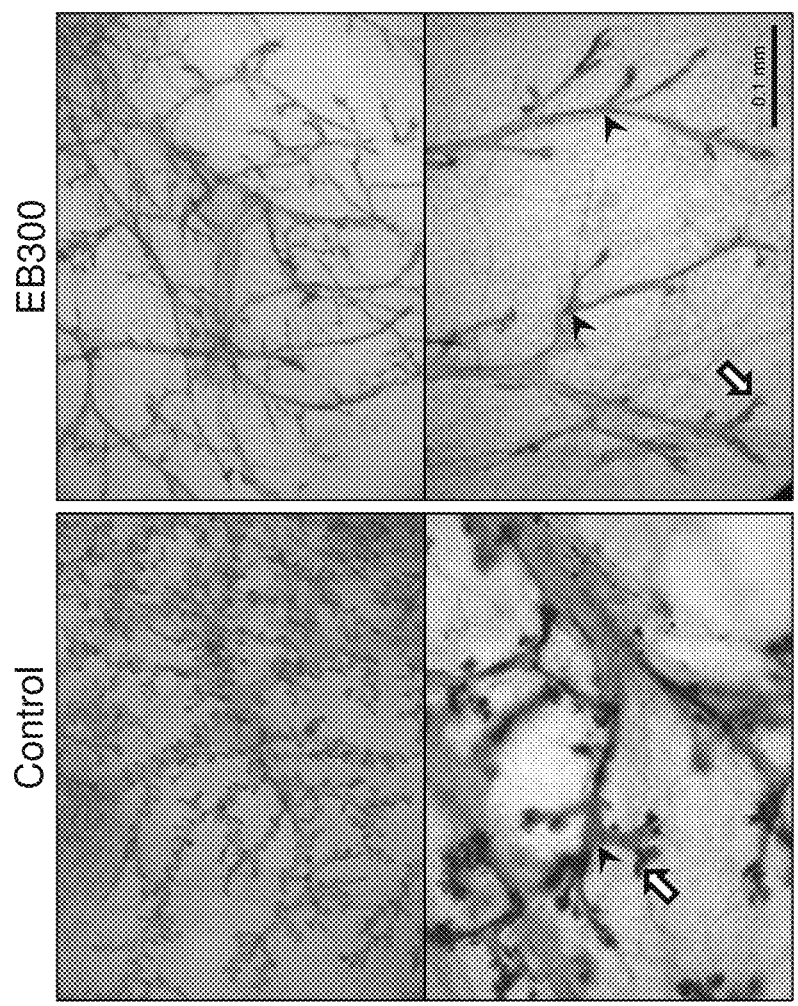

FIG. 23 shows representative mammary glands in females. Fourth mammary glands were dissected from female rats and subjected to whole-mount histological analysis. Tissues were fixed in Carnoy's solution and stained with Carmine alum solution followed by washing with acidic ethanol. Arrowheads indicate mammary gland branching points. Arrows indicate mammary buds.

Figure 24:
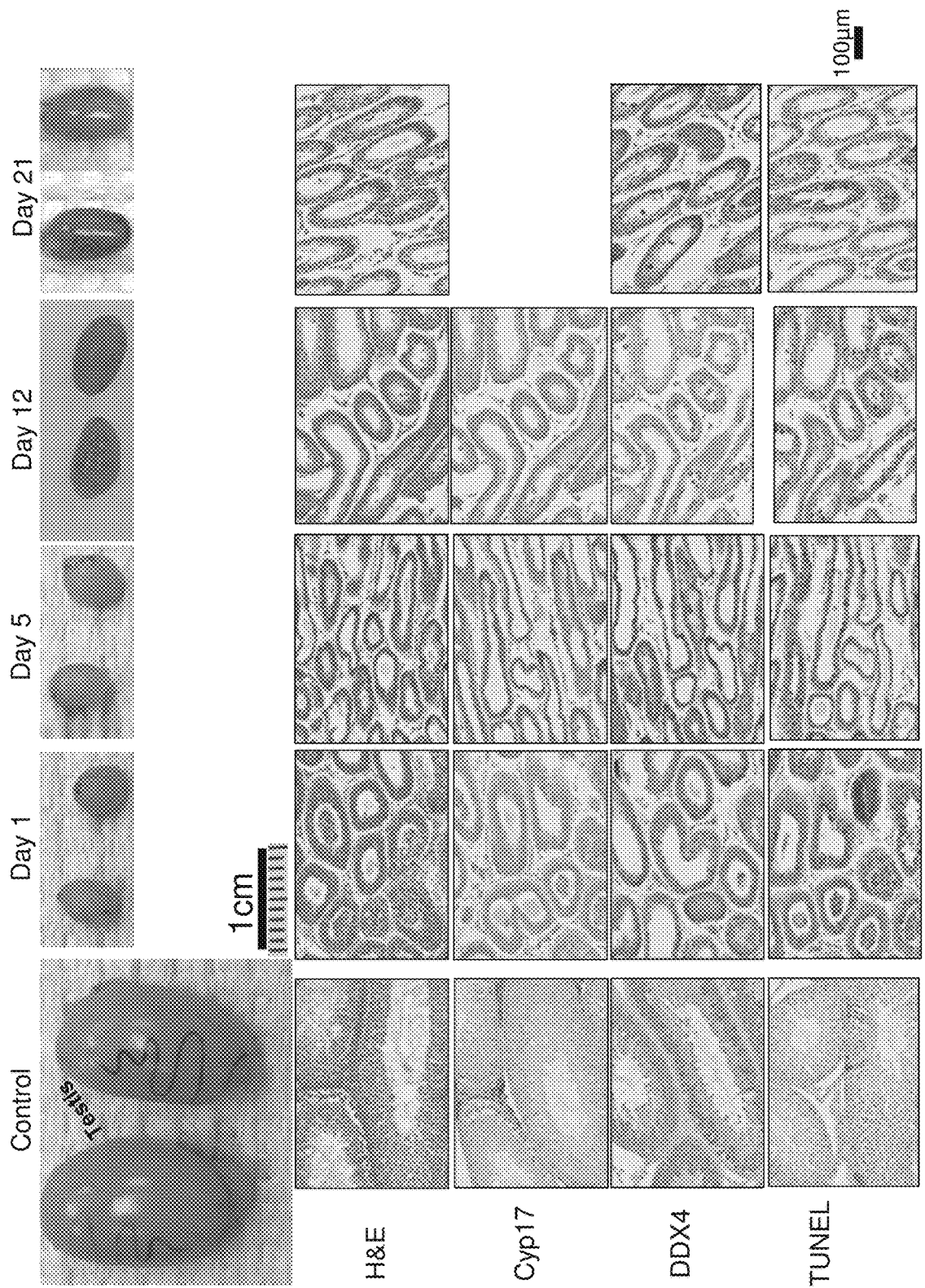

FIG. 24 depicts the effective temporal window in males (testis). Rat male pups were implanted with EB300 on the indicated day of age, and their gonads were dissected and examined at three months of age.

Figure 25:
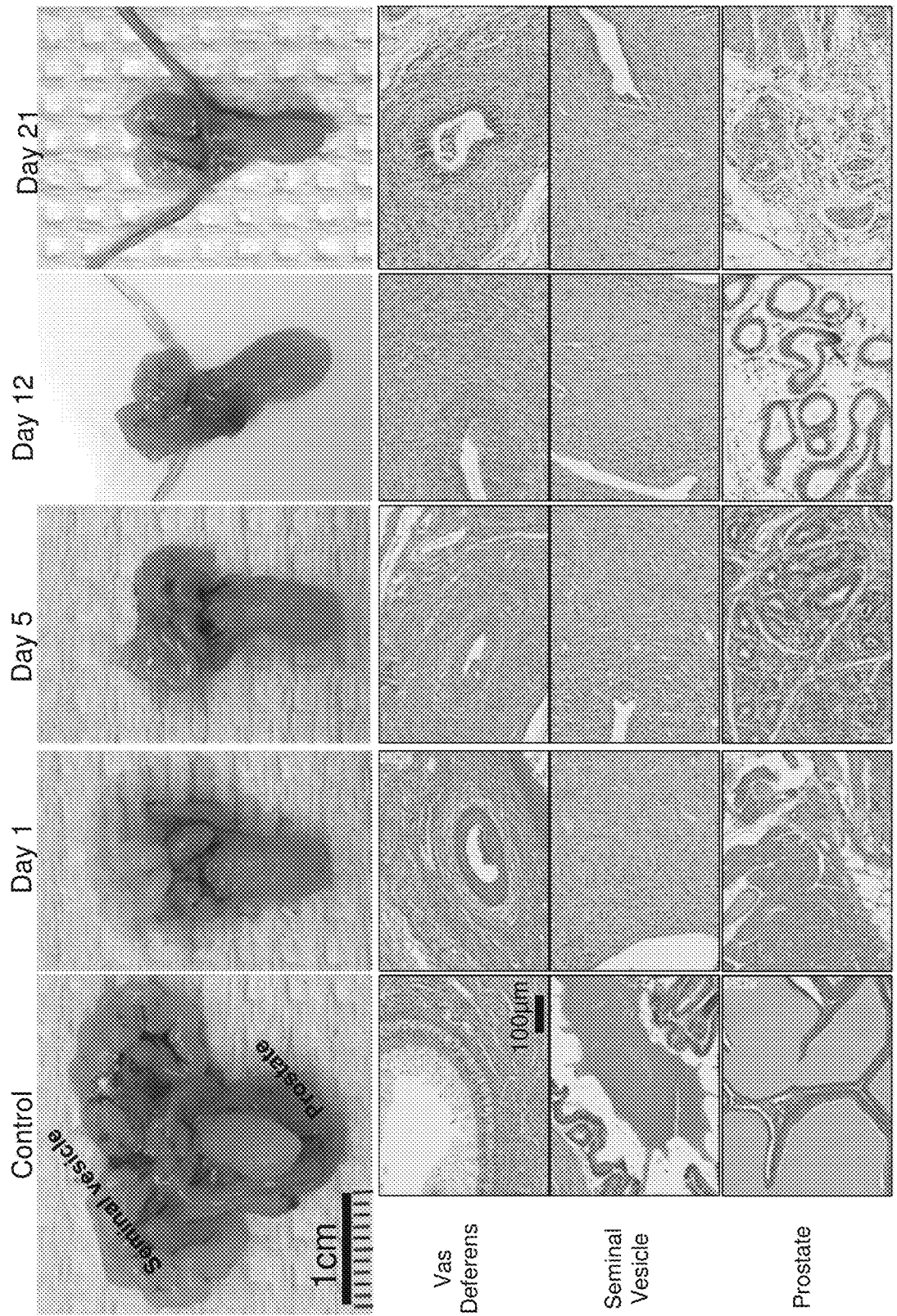

FIG. 25 depicts the effective temporal window in males (repro tract). Rat male pups were implanted with EB300 on the indicated days of age, and their gonads were dissected and examined at three months of age.

Figure 26:
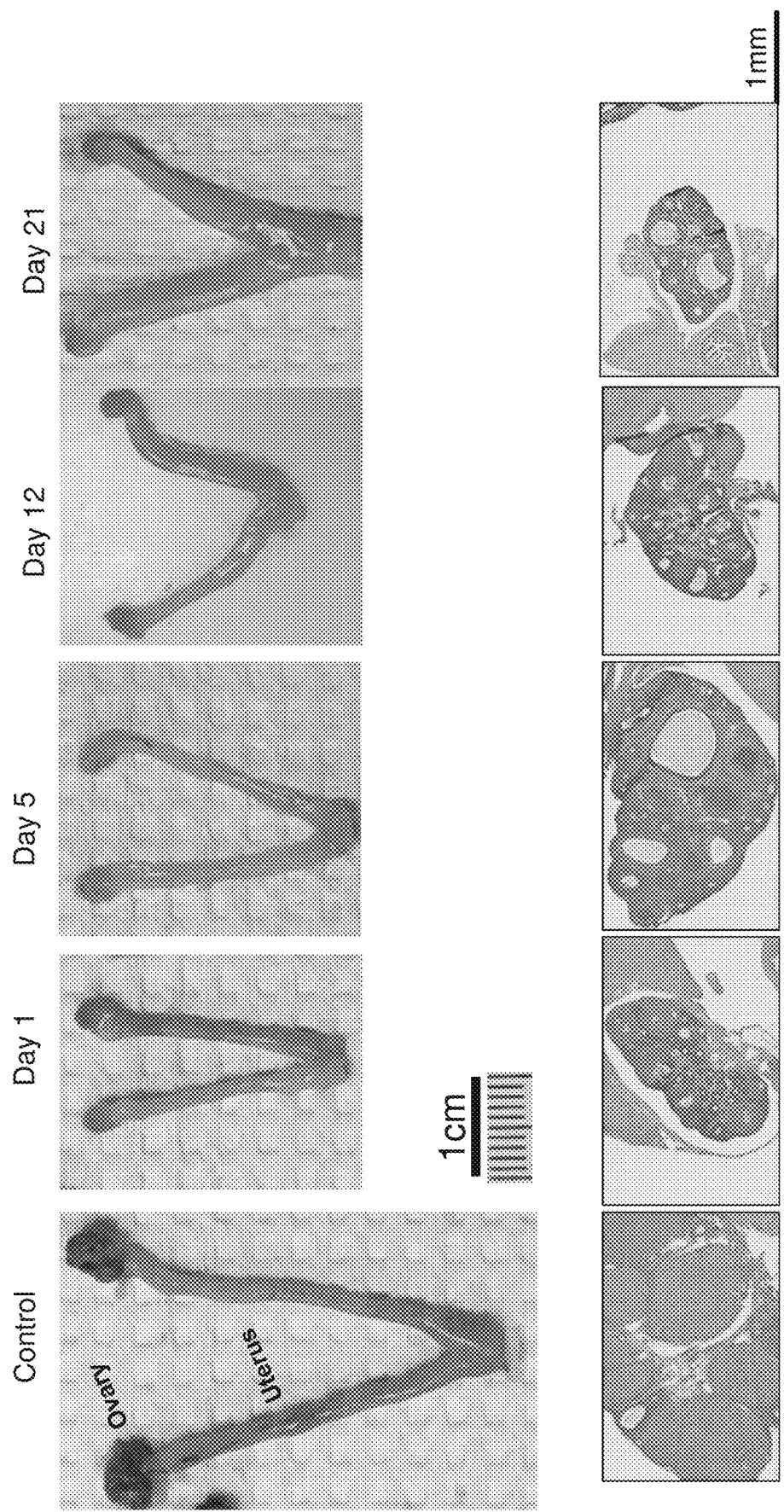

FIG. 26 depicts the effective temporal window in females. Rat female pups were implanted with EB300 on the indicated days of age, and their gonads were dissected and examined at three months of age.

Figure 27:
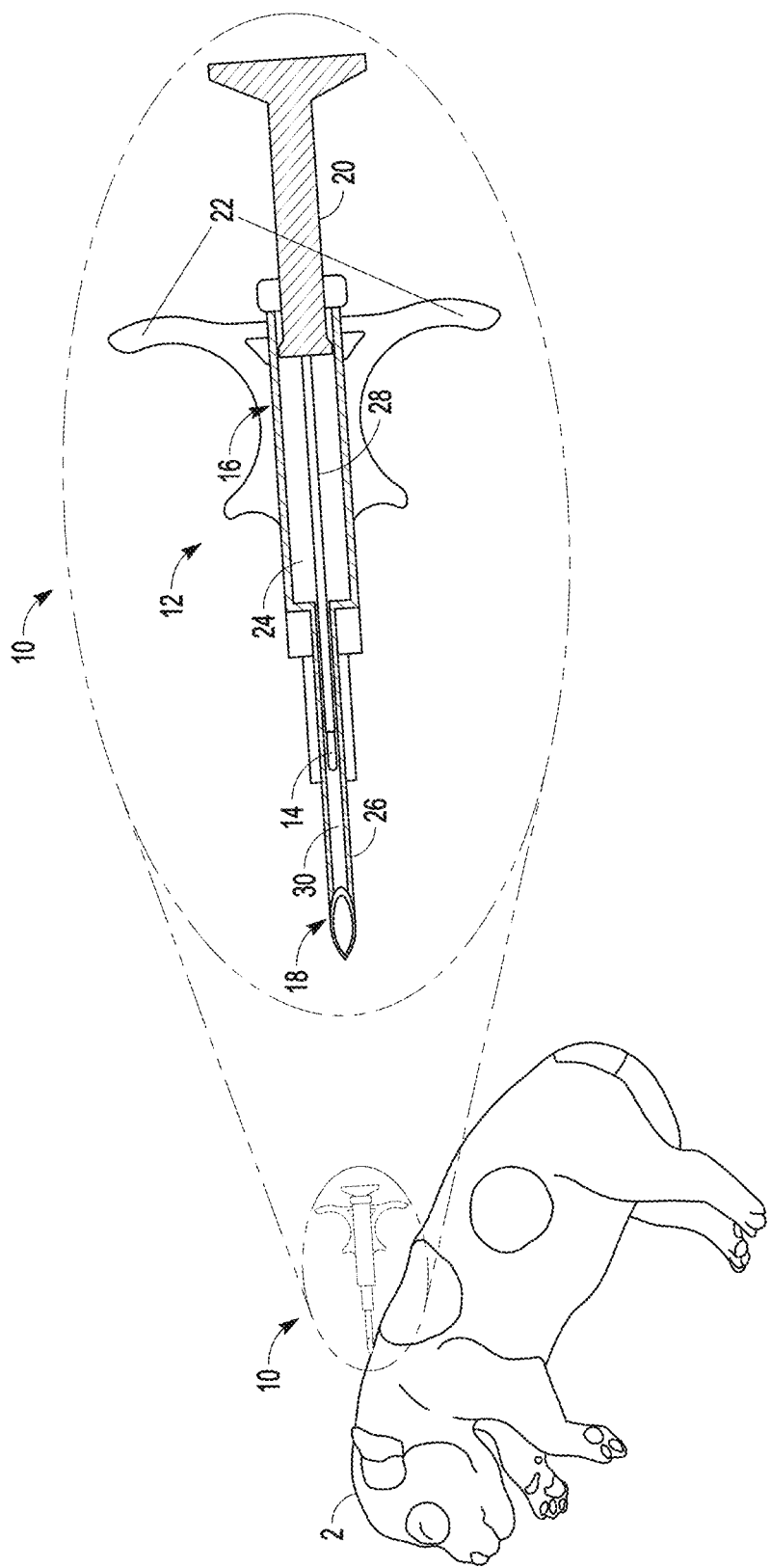

FIG. 27 is a cross-sectional side view of an example injector device for use in a chemical-sterilant delivery system (for example, subcutaneous delivery to a puppy/neonatal canine).

Figure 28:
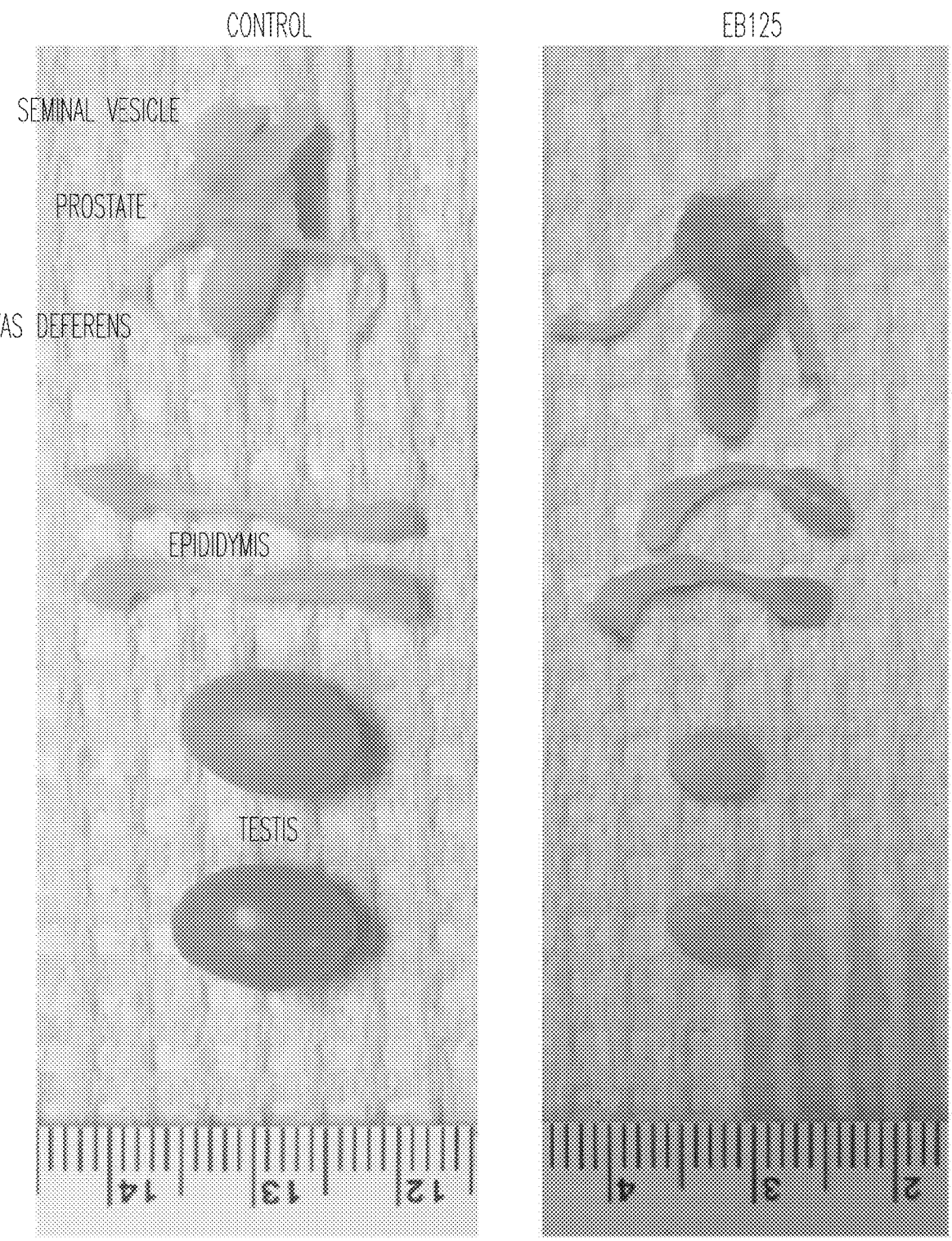

FIG. 28 demonstrates the impact of EB125 on gonadal development in hamsters. Twenty-one-day-old hamsters were implanted either with an empty capsule (control) or 125 micrograms of EB contained in a silastic capsule (EB125). Reproductive tissues were collected from the hamsters at PND30.

DETAILED DESCRIPTION

The following detailed description includes references to the accompanying drawings, which form a part of the detailed description. The drawings show, by way of illustration, specific embodiments in which the invention may be practiced. These embodiments, which may also be referred to herein as "examples," are described in enough detail to enable those skilled in the art to practice the invention. The example embodiments may be combined, other embodiments may be used, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

In this document, the terms "a" or "an" are used to include one or more than one and the term; "or" is used to refer to a nonexclusive "or" unless otherwise indicated. In addition, the phraseology or terminology employed herein and not otherwise defined is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

The term "about" as used herein can allow for a degree of variability in a value or range—for example, within 10%, within 5%, within 1%, within 0.5%, within 0.1%, within 0.05%, within 0.01%, within 0.005%, or within 0.001% of a stated value or of a stated limit of a range—and includes the exact stated value or range.

As used herein, a "subject" is an animal. Animals include mammals, including companion animals such as dogs or cats; farm animals such as equine, bovine, or swine; laboratory animals such as a mouse or rat; as well as non-human primates and humans. The subject also includes an avian.

The term 'infertility" or "sterility" refers to the state of not being fertile or not being able to conceive offspring. Infertility may occur in either the male or the female or both.

As used herein, an "effective amount" means an amount sufficient to induce infertility (i.e., make the animal sterile). An effective amount can be administered in one or more administration. In some embodiments, an effective amount of EB can be achieved in conjunction with another drug, compound, or pharmaceutical composition. In other embodiments, an effective amount of EB may be achieved in isolation from the use of another drug, compound, or pharmaceutical composition.

As used herein, the word "eSpay" refers to any embodiment of the compositions and/or methods using EB as described herein.

The terms "carrier," "pharmaceutically acceptable carrier," or "physiologically acceptable carrier" as used herein refer to one or more formulation materials suitable for accomplishing or enhancing the delivery of EB as a composition (i.e., pharmaceutical composition).

Compositions and Methods

Described herein are compositions that comprise estradiol benzoate (EB) and methods to use estradiol benzoate as a sterilant/inducer of infertility in an animal. Other compounds that may be used in the methods described include, but are not limited to, estradiol, estradiol dipropionate, estradiol valerate, estradiol cypionate (such that any form of chemical compound that releases estradiol or functionally acts like estradiol in vivo may be used). EB has the following structure:

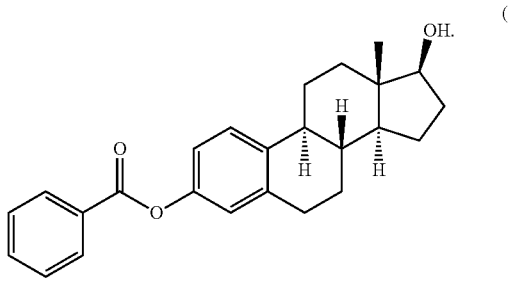

Concentration/Amount of EB

Sterilant (inducing infertility) compositions comprise an infertility-inducing amount of EB. An effective amount of EB to induce infertility can depend, for example, upon the route of administration, the age of the animal, and its size (body weight). Accordingly, the skilled artisan may titer the dosage and modify the route of administration of EB to obtain the optimal effect for a particular animal. A typical dosage of EB may range from about 0.01 mg/kg to up to about 100 mg/kg or more. In other embodiments, the dosage of EB may range from 0.1 mg/kg up to about 100 mg/kg; or 1 mg/kg up to about 100 mg/kg; or 5 mg/kg up to about 100 mg/kg. For example, in rats and hamsters, 300, 100 or 30 µg can be administered to induce infertility. In larger animals, a similar dose would be effective.

Timing of Administration

Compositions comprising EB to induce sterility are administered prior to puberty (prior to reaching sexual maturity/capable of reproduction). The compositions can be administered days, weeks, months, or even years after birth, as long as the compositions are administered before the animal reaches puberty. Administration of EB effectively inhibits/blocks maturation of sex organs/gonads.

Route of Administration

The route of administration of the composition provided herein is in accordance with known methods, e.g., injection (intraperitoneal, intramuscular, subcutaneous) and nasal (inhalation). In one embodiment, EB is administered for sterilization of an animal in a single, one-time dose. In other embodiments, multiple administrations of EB can be carried out to produce sterilization.

Compositions

In one embodiment, EB compositions for injectable administration can be in the form of oleaginous suspensions, including oil, such as vegetable oil (e.g., corn oil), cottonseed oil, peanut oil, and/or sesame oil. Other carriers or fillers can be used instead of, or in addition to, oil. Carriers/fillers can include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. These suspensions can be formulated according to methods available to the art for dispersing and suspending ingredients.

In another embodiment, the composition described above can be encapsulated for administration. In one embodiment, a capsule can be formed from silicone tubing with plugs at each end to contain a mixture of, for example, EB and oil. The capsules can be placed, such as by injection (further described below), in the body of the subject. The EB compositions described herein can be formulated for immediate release or in a time release formulation (e.g., slow release). For example, EB can be prepared with carriers that protect EB against rapid release, such as a controlled release formulation.

Many methods for the preparation of controlled/slow release formulations are known to those skilled in the art. For example, techniques for formulating a variety of sustained- or controlled-delivery means, such as liposome carriers, polymers (e.g., ethylene vinyl acetate, polyanhydrides, silicone, polyglycolic acid, collagen, polyorthoesters, polylactic acid and polylactic, polyglycolic copolymers (PLG)), microparticles, nanoparticles or porous beads, and depot injections) are also known to those skilled in the art. For example, see PCT/US93/00829, which describes controlled release of porous polymeric microparticles for the delivery of pharmaceutical compositions. Additional examples of sustained-release preparations include semipermeable polymer matrices in the form of shaped articles, e.g., films or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556, 1983), poly (2-hydroxyethyl-methacrylate) (Langer et al., J. Biomed. Mater. Res., 15; 167-277, 1981; Langer et al., Chem. Tech. 12:98-105, 1982), ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., Proc. Natl. Acad. Sci. USA, 82:3688-3692, 1985; EP 36,676; EP 88,046; EP 143,949.

In some embodiments, the composition has various release rates (e.g., controlled release or immediate release). Immediate release refers to the release of EB immediately upon administration. In another embodiment, immediate release occurs when there is dissolution of EB within 1-20 minutes after administration. Dissolution can be of all or less than all (e.g., about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of EB. In another embodiment, immediate release results in complete or less than complete dissolution within about one hour following administration.

Controlled-release, slow release, or sustained-release refer to the release of an active ingredient, such as EB, from a composition or dosage form in which the active ingredient is released over an extended period of time. In one embodiment, controlled-release results in dissolution of EB within 20-180 minutes after administration. In another embodiment, controlled-release results in dissolution over several hours to a few days or weeks. In another embodiment, EB is released over a period of a few weeks, including about 15 to 20 days.

In another embodiment, the composition is formulated for inhalation; for example, EB can be formulated as a dry powder. Inhalation solutions may also be formulated with a propellant for aerosol delivery. In another embodiment, inhalation solutions may be nebulized.

One embodiment provides kits for producing a single-dose administration unit. The kits may contain single and multi-chambered pre-filled syringes containing EB and instructions for use (sterilizing an animal).

Delivery System Embodiment

The present disclosure also describes systems and methods for delivering a chemical sterilant composition (also referred to as "a chemical-sterilant delivery system") into an animal to initiate chemical sterilization of the animal. In one embodiment, the sterilant is EB.

FIG. 27 shows a conceptual view of an example chemical-sterilant delivery system 10 (referred to hereinafter as "the sterilant system 10" or simply "the system 10"). This system 10 example includes an injector device 12 (also referred to hereinafter as "the injector 12") that is configured to deliver a sterilant containment body 14 (e.g., capsule) onto or into an animal 2 (shown as a puppy/neonatal canine 2 in FIG. 27, which could be a male or female puppy/neonatal canine). Those having skill in the art will appreciate that the animal 2 could be male or female and could be another type of livestock, such as a piglet or lamb, or could be a companion animal, such as a dog or cat. The sterilant containment body 14 includes a specified dose of the chemical sterilant (e.g., EB) and is configured to release the chemical sterilant into or onto the animal 2 after the sterilant containment body 14 has been delivered to the animal 2 by the injector 12. In an example, the sterilant containment body 14 is generally in the shape of a capsule, e.g., a cylindrical or substantially cylindrical body, so that it can pass through the injector 12 and into or onto the animal 2, as described in more detail below. For this reason, the sterilant containment body 14 will also be referred to as "the sterilant delivery capsule 14," "the delivery capsule 14," or simply "the capsule 14." Those having skill in the art will appreciate that the sterilant delivery body 14 need not have the cylindrical or substantially cylindrical shape that might ordinarily be thought of as a "capsule."

In an example, the injector 12 comprises a main body 16, a force member 20 (e.g., plunger), and, in some examples, an insertion structure 18 and/or one or more grip members 22. In the example shown in FIG. 27, the injector 12 configuration is similar to a medical syringe such that in some examples the injector 12 will be referred to as a "syringe 12," the main body 16 will be referred to as the "barrel 16," and the force member 20 will be referred to as the "piston 20." In an example, the main body 16 at least partially encloses a chamber 24 in which a portion of the force member 20 sits. In an example, the force member 20 can slide along the chamber 24 to change the internal volume experienced by the gas or fluid in the chamber 24 to change the pressure of the gas or fluid in the chamber 24, and thus, to change the driving force exerted by the gas or fluid in the chamber 24.

In an example, the insertion structure 18 (optional) comprises the structure though which the delivery capsule 14 will pass to provide for placement of the delivery capsule 14 at a specified location in or on the animal 2. In an example, the insertion structure 18 comprises a narrow structure with a small cross-sectional area allowing the insertion structure 18 to be used to pierce one or more epidermal layers of the animal 2 so that the delivery capsule 14 can be injected into it. For this reason, the insertion structure 18 may also be referred to hereinafter as "the hypodermic needle 18," or simply "the needle 18." For example, the needle 18 can include a cannula 26 that extends from a proximal end coupled to the barrel 16 and a distal end configured for insertion into the animal 2. The distal end of the cannula 26 can include a relatively sharp pointed tip that can pierce the one or more epidermal layers of the target animal 2. A lumen 30 passes through the cannula 26 from the proximal end to the distal end. In an example, the delivery capsule 14 can be positioned in the lumen 30 where the delivery capsule 14 can be driven out of the cannula 26. In an example, the lumen 30 is in fluid communication with the syringe chamber 24 so that the force member 20, when moved forward, can drive the delivery capsule 14 through the lumen 30 and out the distal tip with sufficient force to be injected into the target animal 2.

The force member 20 includes a movable structure that, when moved from a first position to a second position, can cause the delivery capsule 14 to be moved out of the injector 12 so that the delivery capsule 14 can be delivered into or onto the animal 2. In the example where the injector 12 is a syringe-like device, the main body 16 can be shaped in a cylindrical tube-like configuration, such that the main body 16 may also be referred to herein as "the barrel 16." The force member 20 can comprise a piston that fits tightly within the cylindrical barrel 16 (e.g., with a structure having substantially the same cross-sectional shape and size as a cross section of the barrel 16) so that when the force member 20 is moved axially along the barrel 16, it compresses gas located within the chamber 24 (e.g., air), and the increased pressure acts as a driving force to drive the delivery capsule 14 through the insertion structure 18. In another example, the force member 20 includes a pushing structure 28 that is coupled to or that is part of the piston 20, wherein the pushing structure 28 engages the delivery capsule 14 and pushes the delivery capsule 14 out from the injector 12. For example, if the injector 12 includes an insertion structure 18, then the pushing structure 28 pushes the delivery capsule 14 through the lumen 30 of the insertion structure and out of the distal tip of the cannula 26 for insertion into the target animal. In an example, the one or more grip members 22 are disposed on the main body 16 of the injector 12 and allow a user to hold and stabilize the injector 12 while actuating the force member 20 to drive the delivery capsule 14 into the target animal 2.

In an example, the delivery capsule 14 is sized and shaped so that it fits within the lumen 30 in the insertion structure 18. In an example, the delivery capsule 14 is sized and shaped for intramuscular, intraperitoneal, or subcutaneous injection into the animal 2.

The sterilant system 10 shown in FIG. 27 has been found to be effective in providing for chemical-based sterilization of mammals. For example, in experiments (described in more detail in the EXAMPLES below and as mentioned above) where the sterilant delivery capsule 14 containing a sterilant composition 34 that includes estradiol-benzoate was injected subcutaneously to premature male rats, the sterilant composition 34 was found to be effective in inhibiting development of the neuron Kisspeptin in the hypothalamus of the brain, the testes (e.g., the site of testosterone and sperm production), and the seminal vesicle and prostate (e.g., accessory male reproductive glands that produce semen components). The male rats that were injected with the delivery capsule 14 containing EB were prevented from undergoing puberty and became permanently sterile. Specifically, the male rats' testicles did not produce testosterone or sperm. When the sterilant delivery capsule 14 with the estradiol-benzoate sterilant composition 34 was injected into premature female rats, the estradiol-benzoate was found to inhibit the females' reproductive systems, preventing the females from undergoing menstrual cycling and from producing ova.

The subject rats also did not have had any obvious negative health effects as a result of being injected with the estradiol-benzoate via the sterilant delivery capsule 14. An examination of the animals' immune systems, liver, and kidney functions found no clinical pathology in either the male or female subject rats. Moreover, after testing of more than 200 animals with the estradiol-benzoate-containing delivery capsule 14, no subject animal died or exhibited sickness during a six-month testing period.

The development and function of the reproductive system is consistent throughout all mammalian species. All mammals use the same reproductive hormones with minimal variations among species. For example, reproductive hormones such as estrogen, progesterone, Kisspeptin, luteinizing hormone (LH), and follicle stimulating hormone (FSH) extracted from one species have the same or substantially similar biological effect in all or nearly all other mammalian species. Because of the high level of conservation, estradiol-benzoate sterilant composition 34 (and other estradiol type compositions) will be effective in sterilizing all mammals and avians.

EXAMPLES

Various embodiments can be better understood by reference to the following Examples, which are offered by way of illustration. The disclosure is not limited to the Examples given herein.

Example 1

An eSpay implant induces permanent sterility in males and females.

Introduction

In mammals, Kisspeptin initiates puberty by directly stimulating release of Gonadotropin-releasing hormone (GnRH), also known as gonadoliberin. Thus, Kisspeptin facilitates the correct timing of puberty and normal gonadal development. Knockout of a Kiss1 gene, responsible for encoding Kisspeptin, or its receptor, GPR54, has been found to result in sterility in both male and female mice (with the mouse being used as a model organism). Kisspeptin is expressed primarily in two regions of the hypothalamus, the preoptic area (POA) and the arcuate nucleus (ARC). Whereas Kisspeptin neurons in the POA are thought to have a critical role in luteinizing hormone surges in females, arcuate nucleus Kisspeptin neurons mediate negative feedback effects of steroids on GnRH release in both males and female adults. Although Kisspeptin in prepubertal mammals is necessary to initiate puberty, the contribution of specific populations, whether originating from the arcuate nucleus or preoptic area, is still unclear.

The development of a Kisspeptin neuron and expression of Kisspeptin likely differs between the POA and the ARC. In the preoptic area, Kiss1-expressing cells appear between postnatal days (PND) 8-10 in both sexes of laboratory animals (mice and rats). Sexual dimorphism is revealed at 10-12 postnatal days, where females present more Kisspeptin cells than males in the preoptic area. In contrast, Kisspeptin in the arcuate nucleus is expressed during embryonic development. In both sexes, messenger RNA and protein expression appear around embryonic day 14.5, increasing through embryonic day 18.5, and falling just before birth. Arcuate Kiss1 messenger RNA is detected at postnatal day 0 as soon as 0-4 hours after birth. Unlike in the preoptic area, arcuate Kiss1 is typically expressed in the first ten days of life in rodents. Expression then decreases during the third postnatal week but begins to show increases at puberty.

In further contrast to the expression in the preoptic area, arcuate Kisspeptin expression is not highly sexually dimorphic in adults, compatible with the function of mediating negative feedback that occurs in both sexes. It has been found that arcuate Kisspeptin expression seems to increase around the time of early puberty onset in both sexes. In the female rats, for example, both Kiss1 messenger RNA and neuron fiber density increase prior to puberty onset, with increases occurring first in the arcuate nucleus and later in the preoptic area. This suggests that Kisspeptin in the arcuate nucleus may be responsible for pubertal onset.

Sex steroids appear to be necessary for proper development and organization of Kisspeptin neurons as well as for Kiss1 expression. In Kisspeptin cell-specific estrogen receptor-alpha knockout mice, the number of Kisspeptin fibers in the hypothalamus is reduced. This is also true when hormones are depleted by gonadectomy in developing rodents. Estrogen and testosterone inhibit Kiss1 expression in the arcuate nucleus but increase Kiss1 expression in the preoptic area. It has been found that Kisspeptin neurons may colocalize with estrogen receptors; also, before puberty, estrogen signaling may repress Kisspeptin in the arcuate nucleus, which could interrupt activation of the hypothalamic-pituitary-gonadal (HPG) axis, thereby preventing premature onset of puberty.

Further, exposure of a female to estrogen during postnatal days 0-10 can result in permanent suppression of Kisspeptin expression in the arcuate nucleus. The rats reportedly did not exhibit luteinizing hormone secretion or estrous cyclicity. Though GnRH was produced, its release appeared to be disrupted. The number of observed Kiss1-expressing and Kisspeptin-immunoreactive cells was significantly reduced. However, it is unclear whether the estrogen exposure affects Kisspeptin neuron proliferation and differentiation or transcription and expression of the Kiss1 gene.

Materials and Methods

Animals. Three-month-old Sprague-Dawley male and female rats were purchased from Charles River Laboratory and used as breeders. The newborns were designated as successive breeders if not used for experimental purposes.

When breeders reached breeding age (six weeks old for females and ten weeks old for males), breeding pairs were set up in individual cages for continuous breeding until the desired number of pups was produced or breeders reached one year of age. Pregnancy was indicated by the change of female breeder's body weight and belly bulge. At birth, (post-natal day or PND 0), pups were sexed and assigned to specific experiments. Pups were weaned when they reached the age of 21 days.

Implanting estradiol benzoate capsule. EB powder (17β-Estradiol 3-benzoate, Sigma E8515) was dissolved in sesame oil (Sigma S3547) to make a solution of 300 µg/5 µl concentration. A capsule of EB-300 µg (EB300) was made using silicone tubing (Dow Corning 508-005) containing 5 µl of EB solution that was then sealed with silicone sealant (Factor II, Inc. Medical Adhesive A-100). The capsule (herein called EB300 or eSpay) was left at room temperature for one hour to allow the sealant to dry and then dipped in sesame oil. The size of the capsule was 8 mm long and 2.16 mm in diameter. The skin of the implant site (on the back between the shoulders) was disinfected by applying a povidone-iodine solution. A 2-mm-long transverse incision on the skin was cut with sterile surgical scissors on the back near the shoulder. A packet was created between the skin and muscle layers by inserting the tip of blunt-ended forceps. The capsule was inserted into the pocket and pushed sideways so that the capsule pointed away from the incision. The incision was sealed by applying surgical adhesives.

Hormonal measurement. Blood was collected from the tail vein or by cardiac puncture. The blood was centrifuged at 2000×g for 10 minutes; then serum was collected and preserved at −20° C. until further analyses. Serum estradiol concentrations were measured by using ELISA kits (DRG EIA4399) with a reportable range of 1.4-200 µg/ml. ELISA kits (DRG EIA1559) with a reportable range of 0.083-16 ng/ml were used to measure the concentrations of circulating testosterone. Serum luteinizing hormone (LH) concentrations were measured at the University of Virginia Center for Research in Reproduction Ligand Assay and Analysis Core by a sandwich immunoassay using monoclonal antibodies against both the bovine LH (no. 581B7) and the human LH-beta subunit (no. 5303: Medix Biochemica, Kauniainen, Finland) as previously described (PMID:8462469), with a reportable range of 0.04-37.4 ng/mL.

Testing male mating behavior. To investigate the sexual behavior, four-month-old male rats a were paired with estrus-induced ovariectomized females. Estrus was induced by treatment with exogenous estradiol (50 µg/kg s.c., 54 h before the tests) and progesterone (2.0 mg/kg s.c., 6 h before the tests). The male sexual behavior was observed in a fresh clear cage (56×35×31 cm) illuminated by a 40 W lamp with a red filter. Each naive male rat was individually placed in a testing cage for five min. A receptive female was then introduced, and the sexual behavior was observed for 30 min. The time to first mount (latency) and the number of mounts were recorded for each animal as described previously (PMID:17016704).

Sperm analysis. The cauda epididymis was excised and minced with fine scissors in a warm (37° C.) phosphate buffered saline. The sperm suspension was incubated at 37° C. for ten minutes to allow spermatozoa to swim out of the minced epididymis. Sperm motility was then analyzed by a computer-assisted sperm analyzer (CASA; Sperm Vision II, Minitube of America, Vernon, Wis., USA). At least ten microscopic fields covering the entire viewable area of the semen analysis chamber without overlapping successive fields were examined. Sperm motility was measured by the percentage of motile sperms, progressive motile sperms, and immotile sperms. For total sperm counts, two aliquots of semen samples were collected from each mouse and diluted in 1:200 of formalin for immobilization. Sperm numbers were counted using a hemocytometer, and the average number of sperm concentration per milliliter was calculated and reported as million sperm/mL.

Hypothalamic-pituitary responsiveness upon KISS-10 injection. Peripheral blood (50 µL) was collected from the ventral tail vein in adult male and female rats aged 60-70 days. Immediately after blood collection, the rats were intraperitoneally injected with 50 nmole/animal Kisspeptin-10 (Metastin 45-54, Millipore-Sigma, San Diego, Calif.), and another blood sample was collected 30 minutes post-injection. Samples were centrifuged at 2000×g for ten minutes, and serum was collected and stored at −20° C. until further analyses. Serum luteinizing hormone (LH) concentrations were measured at the University of Virginia Center for Research in Reproduction Ligand Assay and Analysis Core by a sandwich immunoassay using monoclonal antibodies against both the bovine LH (no. 581B7) and the human LH-beta subunit (no. 5303: Medix Biochemica, Kauniainen, Finland) as previously described (PMID: 8462469), with a reportable range of 0.04-37.4 ng/mL.

Fertility test. To assess fertility of the male rats, each one was housed with a breeder female for two weeks at the age of four months. The male fertility percent (number of males that produced a litter/total number of males×100) and litter size (number of pups per litter) were recorded. To assess fertility of the female rats, each female rat was housed with a breeder male for two weeks at the age of three months. The female fertility percent (number of females that produced a litter/total number of females×100) and litter size (number of pups per litter) were recorded.

Histopathology. At their respective sampling ages, rats were euthanized by $CO_2$ asphyxiation followed by bilateral thoracotomy. Whole or portions of organs (brain, pituitary, gonads, reproductive tract, heart, liver, kidney, spleen, mammary glands, and femur) were dissected out and immediately fixed in freshly prepared 4% paraformaldehyde for 24 hours, followed by wash in PBS (phosphate buffered saline pH 7.4) and then stored in 70% ethanol at 4° C. until use. Fixed tissues were processed via automated tissue processor (Miles Scientific Tissue Tek VIP 2000) and embedded into paraffin blocks. Embedded tissues were cut into 7 µm-thick sections using a microtome (Leica Biocut Model 3011) and mounted on positively charged glass slides (type). After deparaffinization, the tissue was processed for either hematoxylin and eosin staining or immunohistochemistry (IHC) for various biomarkers. Antigen retrieval for IHC was done using Citrate buffer (pH 6.0) and microwaved at 10% power for 15 minutes. Endogenous peroxidase activity was blocked using 3% $H_2O_2$ for 20 minutes, and slides were blocked with 5% host serum for one hour before incubating with primary antibodies overnight at 4° C. The following primary antibodies were used: Kisspeptin (Rabbit-anti-kisspeptin 1:250, AB9754-Millipore-Sigma), DDX4/MVH (Rabbit-anti-DDX4/MVH 1:2,000, AB13840 Abcam), LHβ (Rabbit-anti-LHβ 1:100, National Hormone & Peptide Program), StAR (Rabbit-anti-StAR 1:2,000, SC-25806 Santa Cruz), GH (Rabbit-anti-GH 1:100, National Hormone & Peptide Program), Cyp17A1 (Rabbit-anti-bovine Cyp17A1 1:5,000, a gift from Dr. Alan Conley at UC Davis). Peroxidase conjugated donkey or goat anti-rabbit secondary antibodies were used at 1:200 concentration and detected using a DAB kit (VectorLabs). Whole mount mammary gland preparation and analysis was done as previously described (10.21769/

BioProtoc.2915). An apoptotic assay was performed by using an in situ apoptosis detection kit S7100 (Millipore) stained with DAB chromogen (diaminobenzidine) and counterstained with hematoxylin according to the manufacturer's instructions.

Hemato-biochemistry. Blood was collected by cardiac puncture and immediately split into two samples: (a) For the complete blood count (CBC), blood was mixed with EDTA in a hematological tube (BD Microtainer 365967) and stored at 4° C. before analysis within 24 hours. (b) For the serum biochemistry profile, blood was centrifuged at 2000×g for ten minutes; then separate serum was collected and preserved at −20° C. until analysis. Sample analysis was performed by the Veterinary Diagnostic Laboratory at the University of Illinois at Urbana-Champaign.

Single Cell RNA sequencing. To investigate the differential gene expression in the hypothalamus region between the Vehicle and EB300, the hypothalamus was obtained from two rats in each group, and single-cell suspension from the same group was pooled to perform single-cell RNA sequencing (scRNAseq). Blood was removed by perfusion using M199 culture media after euthanization. The brain was quickly dissected and transferred to ice-cold M199 culture media containing 10% FBS. The hypothalamic region was dissected using curved fine forceps. The hypothalamic tissue was dissociated into single-cells using Neural Tissue Dissociation Kit—Postnatal Neurons (Miltenyi Biotec Inc., Auburn, Calif.) according to the manufacturer's instruction. Trypan blue exclusion confirmed viability to be >85% in all samples. Cell suspensions were filtered using a 40 μm filter, and dissociated cells were pelleted and re-suspended in PBS with 1% bovine serum albumin (BSA; Sigma-Aldrich, St. Louis, Mo.). Cellular suspension (about 3000 cells) of each sample was loaded on a 10× Chromium instrument (10× Genomics, Pleasanton, Calif.) according to the manufacturer's protocol. Single-cell RNA-Seq libraries were prepared using the Chromium Single Cell 3' v2 Reagent Kit (10× Genomics) according to the manufacturer's protocol. The initial step performed an emulsion where individual cells were isolated into droplets together with gel beads coated with unique primers bearing 10× cell barcodes, unique molecular identifiers (UMI), and poly(dT) sequences. Reverse transcription reactions were engaged to generate barcoded full-length cDNA followed by the disruption of emulsions using the recovery agent and cDNA clean up with DynaBeads MyOne Silane Beads (Thermo Fisher Scientific). Bulk cDNA was amplified using a GeneAmp PCR System 9700 with a 96-Well Gold Sample Block Module (Applied Biosystems). Amplified cDNA product was cleaned up with the SPRI select Reagent Kit (Beckman Coulter). Indexed sequencing libraries were constructed using the reagents from the Chromium Single Cell 3' v2 Reagent Kit, following these steps: (1) fragmentation, end repair, and A-tailing; (2) size selection with SPRI select; (3) adaptor ligation; (4) post-ligation cleanup with SPRI select; (5) sample index PCR and cleanup with SPRI select beads. Library quantification and quality assessment was performed using a Qubit fluorometric assay (Invitrogen) with a dsDNA HS (High Sensitivity) Assay Kit and Bioanalyzer Agilent 2100 using a High Sensitivity DNA chip (Agilent Genomics). Indexed libraries were equimolarly pooled and sequenced on an Illumina HiSeq4000.

Analysis for scRNA-seq data. Single-cell expression was initially analyzed using the Cell Ranger Single Cell Software Suite (v2.1.1) to perform quality control, sample de-multiplexing, barcode processing, and single-cell 3' gene counting. Sequencing reads were aligned to the UCSC rn6 rat transcriptome using the Cell Ranger suite with default parameters. Samples were merged using cell-ranger aggregate function with default parameters. A total of 3,634 and 3,339 single cells were analyzed from the control and EB300 groups, respectively. Mean raw reads per cell were 45,201 and 48,751 respectively. Median genes per cell were 1,496 and 1,429, respectively. Further analysis was performed in R (v3.5) using the cellrangerRkit (v2.2.0), Seurat (v2.0) and Monocle package (v2.8.0). The gene-cell-barcode matrix of the samples was log-transformed and filtered based on the number of genes detected per cell (any cell with fewer than 300 genes or more than 5,000 genes per cell was filtered out), as were cells with more than 6% of mitochondrial UMI counts and more than 50% of ribosomal UMI counts. Regression in gene expression was performed based on the number of UMI counts and the percentage of mitochondrial genes. Only genes detected in at least three cells were included. Cells were then scaled to a total of 1e4 molecules. Altogether, 6,964 cells were kept for statistical analysis. To reduce data dimensionality, 2,505 variable genes were selected based on their expression and dispersion (expression cut-off=0, and dispersion cut-off=0.5). PCA was run on the normalized gene-barcode matrix. Barnes-hut approximation to t-SNE was then performed on the first 12 principal components to visualize cells in a two-dimensional space. The first 11 principal components were used for the t-SNE projection and clustering analysis using the Elbow Plot approach. Clusters were identified using the "FindClusters" function in Seurat with a resolution parameter of 0.6. This graph-based clustering method relies on a clustering algorithm based on shared nearest neighbor (SNN) modularity optimization. Unique cluster-specific genes were identified by running the Seurat "FindAllMarkers" function using the MAST framework. A total of 17 clusters were identified from tSNE, and five maker genes in each cluster were identified using the "FindMarkers" function. The tSNE plot, histogram, scatter plot, and violin plots were plotted using Seurat.

Statistics

General data analyses were performed using statistical software (SPSS 22). Continuous data were tested for normal distribution by a Shapiro-Wilk test. Following homogeneity of variance confirmation, all normally distributed continuous data were analyzed with parametric tests and a Tukey's HSD post hoc test. All non-normally distributed continuous data were analyzed by non-parametric tests (Kruskal Wallis ANOVA). Ordinal data were similarly analyzed. Data are graphically presented as the mean and standard error of the mean. For all analyses, the alpha value was set to 0.05. For drawing conclusions from scRNAseq, unique cluster-specific genes were identified by running the Seurat "FindAllMarkers" function using the MAST framework. A total of 17 clusters were identified from tSNE; the top five maker genes in each cluster were identified using the "FindMarkers" function. Differential gene expression between control and EB300 was tested by the default 'bimod' likelihood ratio test in Seurat (cut-off, $p\_val\_adj<0.05$). The tSNE plot, histogram, scatter plot and violin plots were plotted using Seurat.

Results

Controlled Delivery of 17β-estradiol 3-benzoate Via eSpay to Neonatal Rats Irreversibly Suppresses Hypothalamic Kisspeptin Expression and Germ Cell Development in Both Males and Females

Fabrication of eSpay (or Alternatively Called EB300)

A silicone capsule containing 17β-estradiol 3-benzoate (EB, Sigma E8515) was used as a device to elevate blood 17β-estradiol (E2) concentration to a supra-physiological level. Once implanted subcutaneously, the silicone capsule with EB (called eSpay) releases EB for an extended period of time. EB was chosen instead of E2 because E2 is rapidly removed by liver metabolism, while EB is slowly hydrolyzed into E2, rendering a sustained, high blood E2 level for an extended period of time of about three weeks. After a number of studies, it was determined that a subcutaneous implant of 300 μg of EB would be effective in inducing sterility. Therefore, EB that contained 300 μg of EB (herein EB300) was made by dissolving 300 μg of EB in 5 μl of sesame oil (Sigma S3547), and it was inserted into a silicone tube (Dow Corning 508-005) that was later closed with silicone sealant (Factor II, Inc. Medical Adhesive A-100). The capsule was kept at room temperature until use. The EB300 capsule was approximately 8 mm long and 2.16 mm in diameter. The skin of implant site (on the back between shoulders) was disinfected by applying povidone-iodine solution. A 2-mm long transverse incision was made on the skin with sterile surgical scissors. A packet was created between the skin and muscle layers by inserting the tip of blunt-ended forceps. The capsule was inserted into the pocket and pushed sideways so that it pointed away from the incision, which was sealed by applying surgical adhesives.

The efficacy of the EB300 capsule as a device to elevate E2 levels in its recipient was tested after implanting it on the day of birth (post-natal day 0, PND 0). Serum and hypothalami were collected at PND 1, 2, 3, 4, 7, 10, 21, and 30, and E2 concentrations were measured. Serum E2 concentration was elevated and maintained at a plateau for 10 days (FIGS. 1A-B) and gradually decreased with time, but it still maintained slightly higher levels in EB-treated groups than untreated controls until PND 30 (FIG. 1A). E2 measured from hypothalami (calculated as if 1 mg tissue volume equals to 1 mL) showed similar elevation patterns, but the concentration was 100 times higher than in the sera and then sharply dropped by PND 4 and returned to close to basal level by PND 7 (FIG. 1B). The same patterns of hormone profiles were seen in males and females (FIGS. 2A-B). These results show that the EB300 implant induces a sustained high level of E2 in the circulating blood for up to about 30 days. Furthermore, the selective increase of hypothalamic E2 levels over the serum levels for the first four days and the sharp decline later when the serum E2 level is still high indicates that the hypothalamus may have a unique regulatory system that temporarily accumulates and removes E2.

Impact of the EB300 Implant on the Hypothalamic Kisspeptin Expression

Neonatal exposure to estrogen significantly reduced the arcuate nucleus (ARC) Kisspeptin immunoreactivity in both males and females in early adulthood at 2.5 months of age (FIG. 3A) and similarly, lower immunoreactivity was seen in the EB300 group at 6-7 months of age (FIG. 3B). In general, males had lower Kisspeptin immunoreactivity than females in both young and older rats, but EB decreased Kisspeptin (KISS, a protein product of Kiss1 gene) immunoreactivity in both sexes. This result shows that an EB300 implant in a neonate decreases the KISS expression, and the effect persisted for a long time. As rats reach puberty by the age of two months, and KISS is the key master hormone in establishing fertility, the decreased KISS impacts fertility in the rats that received EB300 implant.

Figure 4A:
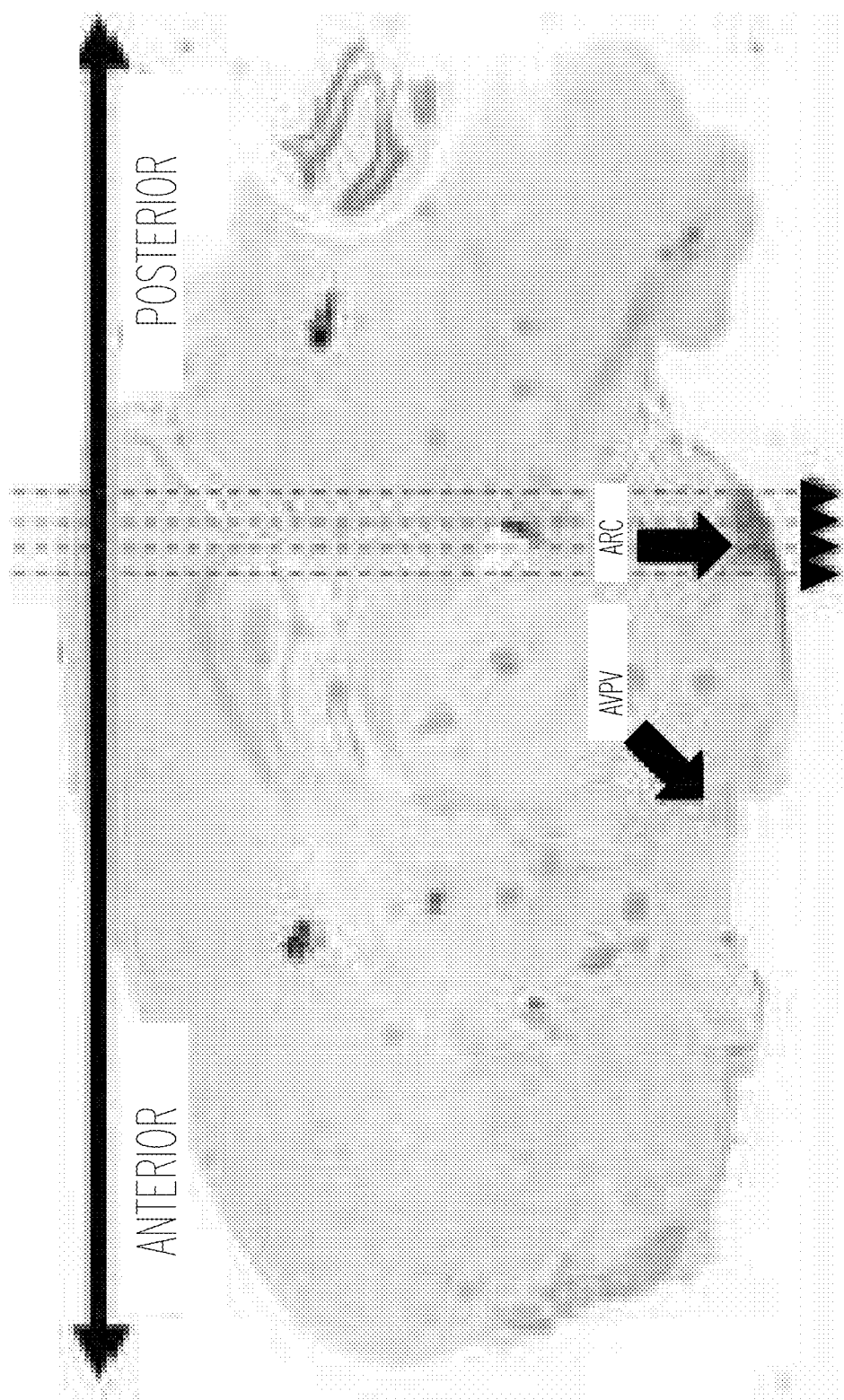
FIGS. 4A-K depict the KISS1 expression pattern and the identification of cells and genes expressed in PND 29 hypothalami of Control (intact) and EB300 implanted rats. KISS1 is expressed in the AVPV and ARC regions (FIG. 4A). KISS1 expression was examined in the ARC region by anti-KISS1 antibody, KISS1 protein (white dots in images) (planes of tissue sections are marked as a red dotted line in FIG. 4A). KISS1 expression was visibly decreased in the EB300 hypothalamus compared to that of the Control group (FIG. 4B; less while signals are in the EB300). To quantitatively measure KISS1 expression between control and EB300 groups, the hypothalamic region including the AVPV and ARC was dissected and examined by single-cell RNA sequencing (scRNAseq) (FIG. 4C). In females, 10 different cell types (cell clusters) were identified (FIG. 4D) from a total of 4,049 and 4,223 cells respectively from the Control and EB300 groups (FIG. 4E). From the hypothalamic cell clusters, a Kiss1-expressing cluster (cluster-9) was identified (FIG. 4F), and the number of Kiss1-expressing cells and expression level of Kiss1 were compared between the Control and EB300 groups. In the cluster-9, 307 and 194 cells were found in the Control and EB300 groups, respectively. Sixty-eight and 30 Kiss1-positive cells were identified from each group, respectively. This result indicates that total cell numbers in cluster-9 and Kiss1-expressing cells were both decreased in the EB300 hypothalamus compared to that of the Control group (FIG. 4G). In males, ten different clusters were identified (FIG. 4H), of which a total of 4,674 and 4,229 cells were examined in the Control and EB300 groups, respectively (FIG. 4I). From the hypothalamic cell clusters, a Kiss1-expressing cluster (cluster-8) was identified (FIG. 4J). The numbers of Kiss1-expressing cells and expression level of Kiss1 were compared between the Intact and EB300 groups. In cluster-8, 178 and 83 cells were found in the Control and EB300 groups, respectively. Sixty-five and 37 Kiss1-positive cells were identified from each group, respectively. This finding indicates that the total cell number in cluster-8 and Kiss1-expressing cells was decreased in the EB300 hypothalamus compared to that of the Control group (FIG. 4K).

Impact of EB300 implant on hypothalamic gene expression. FIGS. 4A-K depict the adult hypothalamus, KISS1 is expressed in the AVPV and ARC regions (FIG. 4A).

Figure 4B:
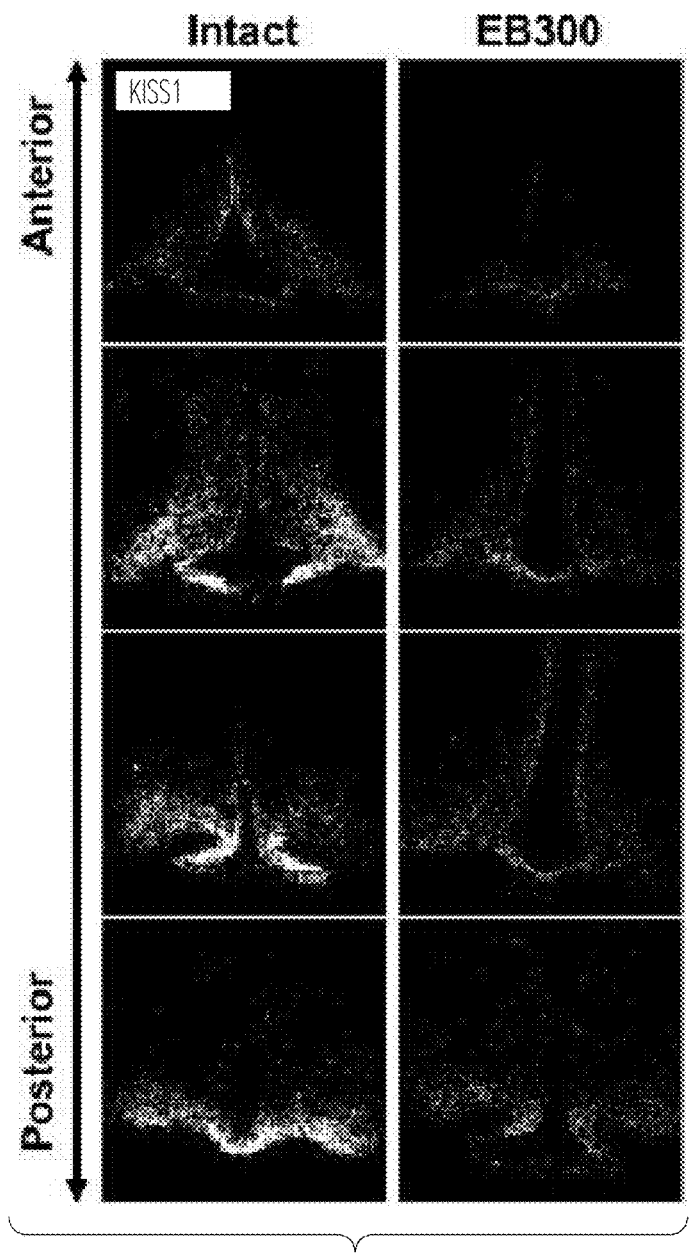
Figure 4C:
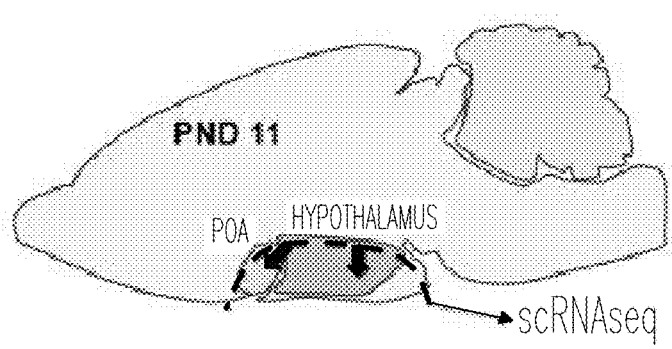
Figure 4D:
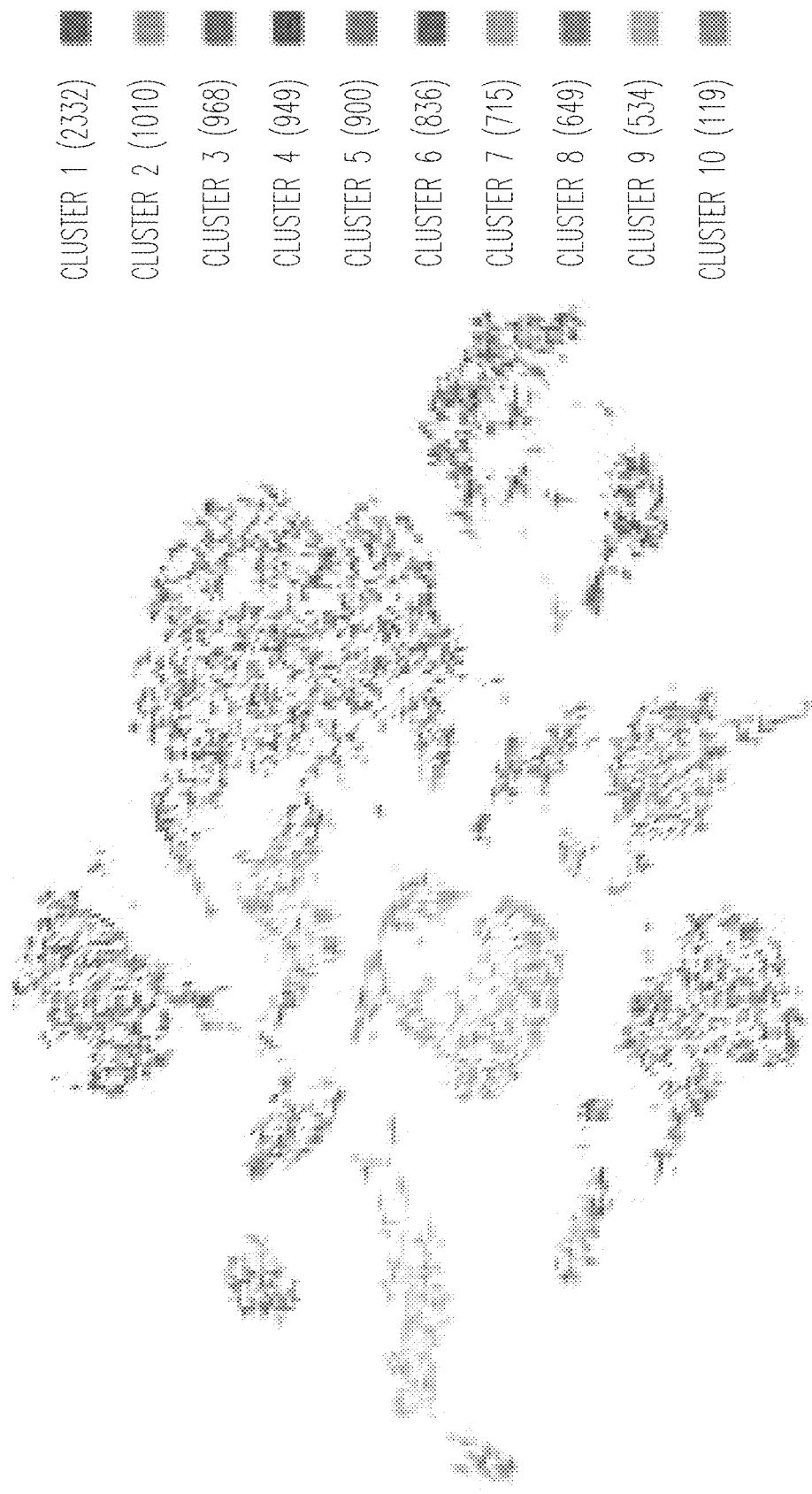
Figure 4E:
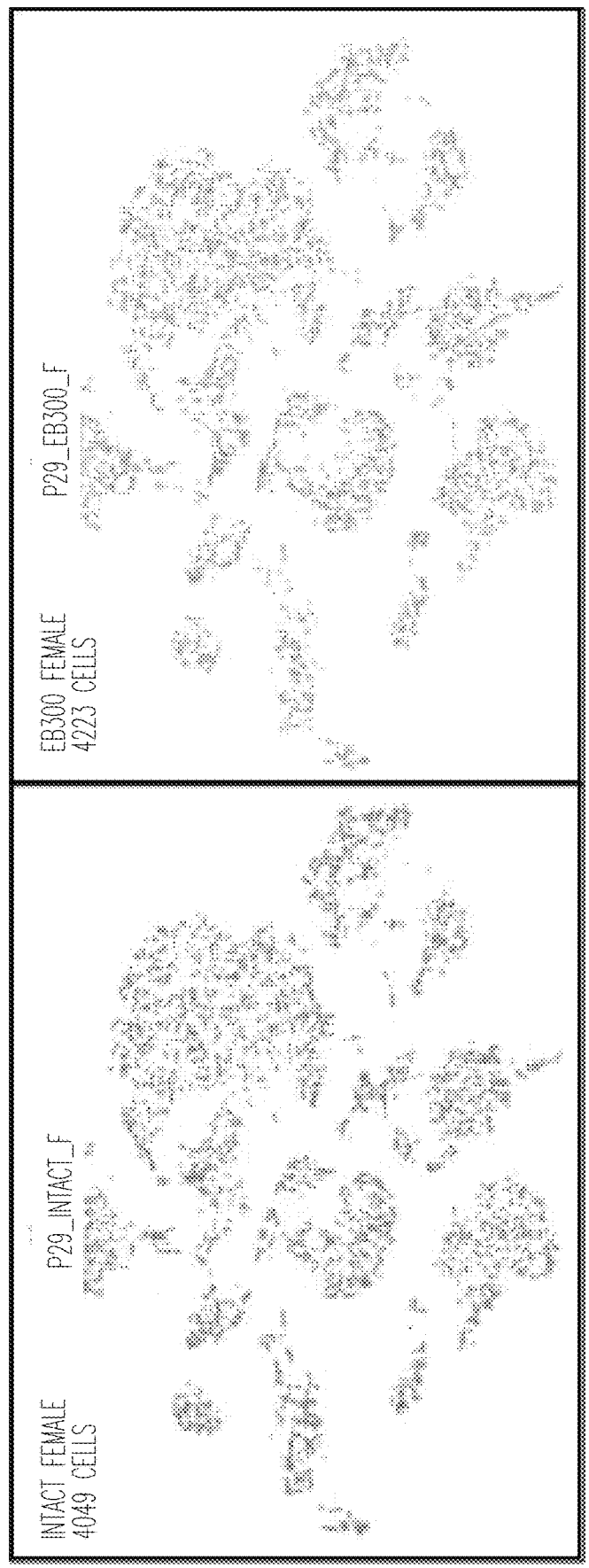
Figure 4F:
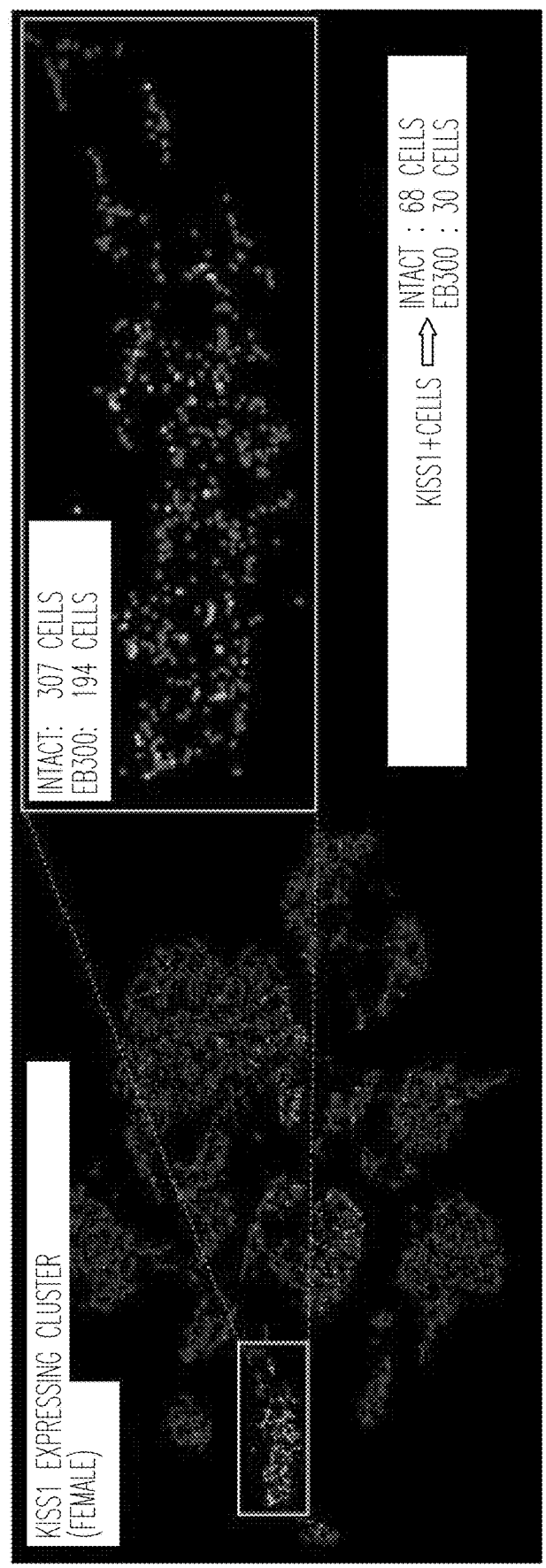
Figure 4G:
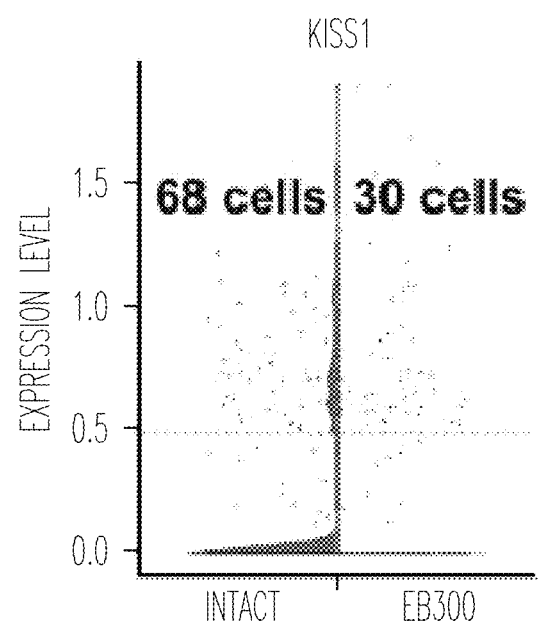
Figure 4H:
Figure 4I:
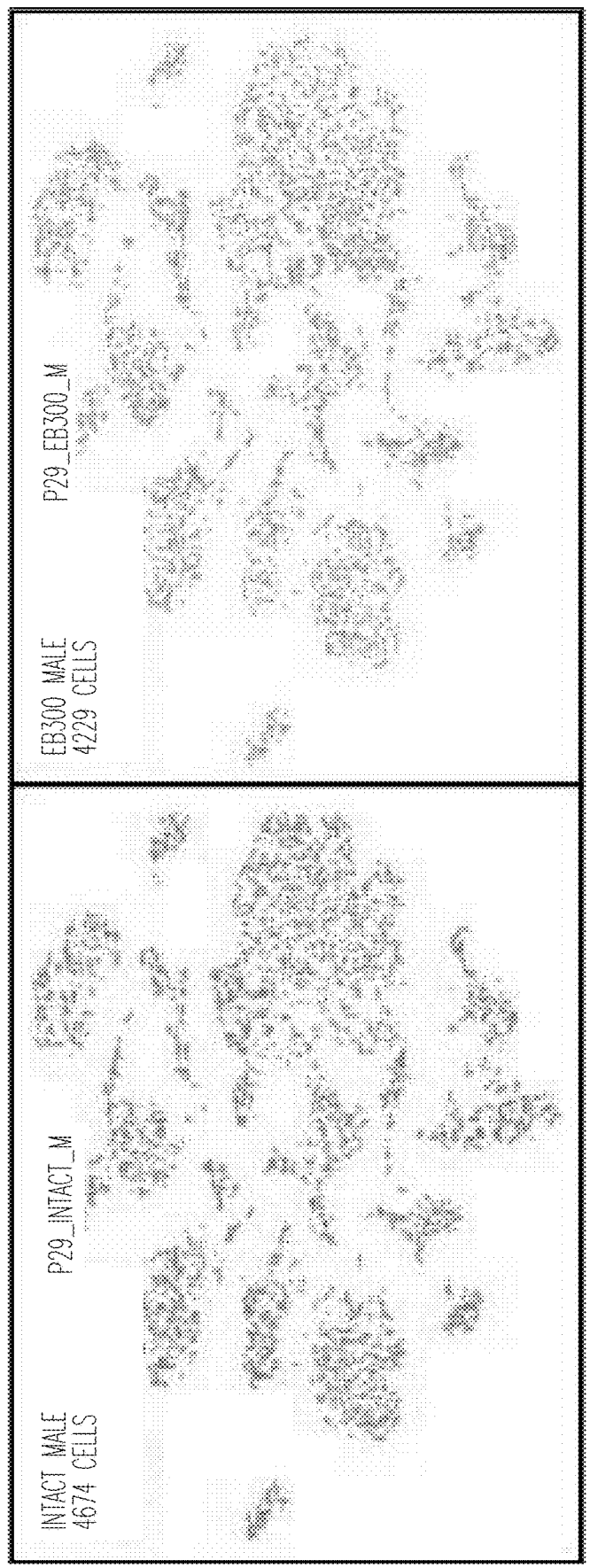
Figure 4J:
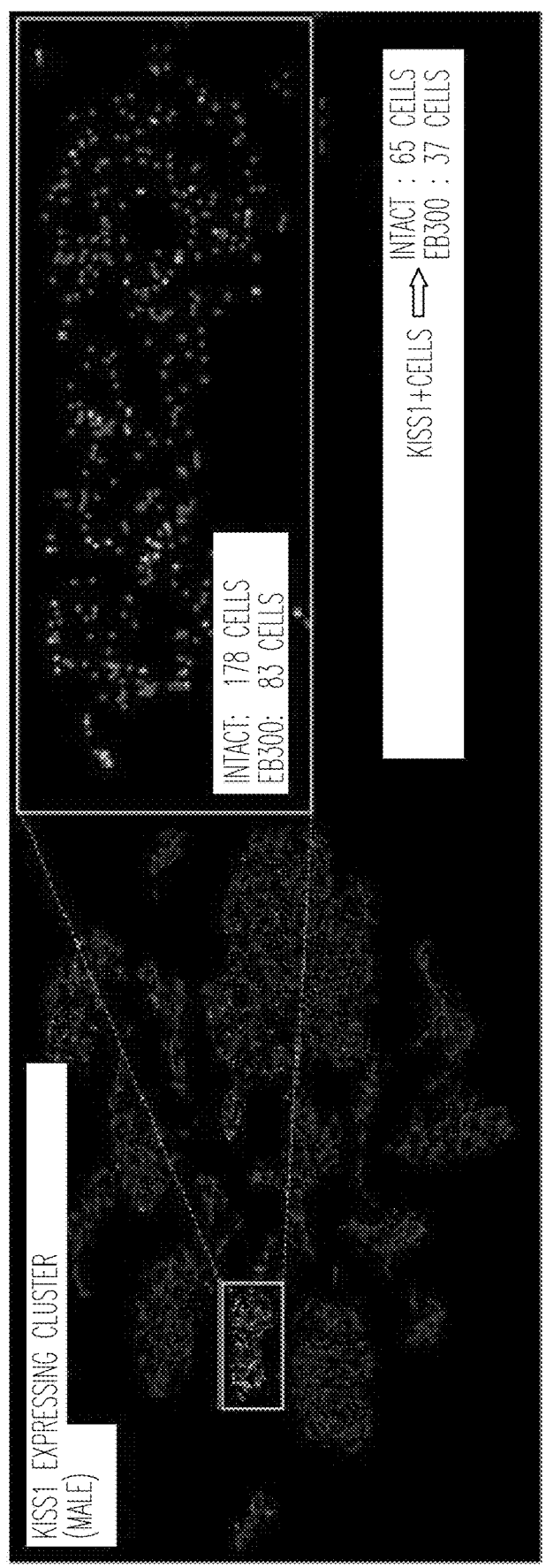
Figure 4K:
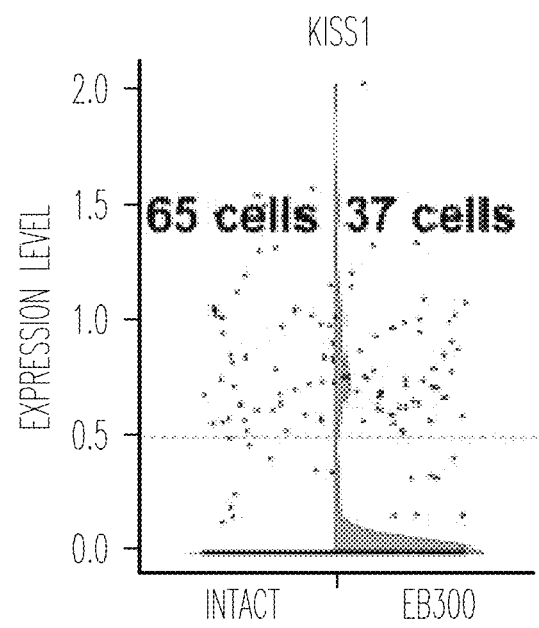

KISS1 is expressed in the AVPV and ARC regions (FIG. 4A). KISS1 expression was examined in the ARC region by anti-KISS1 antibody, KISS1 protein (white dots in images) (planes of tissue sections are marked as red dotted lines in FIG. 4A. The KISS1 expression was visibly decreased in the EB300 hypothalamus compared to that of the Intact (Control) group (FIG. 4B). To quantitatively compare KISS1 expression between the Control and EB300 group, the hypothalamic region (including the AVPV and ARC regions) was dissected and examined by single-cell RNA sequencing (scRNAseq) (FIG. 4C). In females, ten different cell types (cell clusters) were identified (FIG. 4D) from a total of 4,049 and 4,223 cells from the Control and the EB300 groups, respectively (FIG. 4E). From the hypothalamic cell clusters, a Kiss1-expressing cluster (cluster-9) was identified (FIG. 4F), and the numbers of Kiss1-expressing cells and expression level of Kiss1 were compared between the Control and EB300 groups. In the cluster-9, 307 and 194 cells were found in the Control and EB300 groups, respectively. Sixty-eight and 30 Kiss1-positive cells were identified from each group, respectively. This result indicates that total cell numbers in the cluster-9 and Kiss1-expressing cells were both decreased in the EB300 hypothalamus compared to that of the Control group (FIG. 4G). In males, ten different clusters were identified (FIG. 4H), of which a total 4,674 and 4,229 cells were examined in the Control and EB300 groups, respectively (FIG. 4I). From the hypothalamic cell clusters, a Kiss1-expressing cluster (cluster-8) was identified (FIG. 4J). The numbers of Kiss1-expressing cells and expression level of Kiss1 were compared between the Control and EB300 groups. In the cluster-8, 178 and 83 cells were found in the Control and EB300 groups, respectively. Sixty-five and 37 Kiss1-positive cells were identified from each group, respectively. This finding indicates that the total cell number in cluster-8 and Kiss1-expressing cells was decreased in the EB300 hypothalamus compared to that of the Control group (FIG. 4K). Taken together, these results show that EB treatment on neonatal female and male rats decreased the number of KISS1-cells and consequently, KISS1 protein expression, in the hypothalamus.

Impact on the Pituitary

Histopathological analysis of male and female pituitaries was performed to see if the pituitary underwent changes following the injection of EB300 (FIG. 5). Paraffin sections of pituitaries obtained from the Control and EB300 groups were examined by histology by H&E staining, which found no histological differences among the groups. Immunohistochemistry for LHβ (luteinizing hormone β subunit) and GH (growth hormone) found no difference of LH and GH expressions between the control and EB treated groups (FIG. 5). These results indicate that the effect of the EB implant may not impact growth hormone secretion or LH hormone secretion.

LH Secretion Upon KISS-10 Injection

When secreted from a Kisspeptin neuron, KISS binds to its cognate receptor, KISS1R, localized on the GnRH neurons, and stimulates GnRH secretion, which in turn stimulates LH secretion from the pituitary gonadotrophs. To determine if GnRH neurons and gonadotrophs retained their responsiveness and functionality in animals implanted with EB300, serum LH concentrations were measured before and after an injection of Kisspeptin-10 (KISS-10; a 10 amino acid long analog of KISS) in 2.5-month old animals (FIG. 6). Before KISS-10 injection, the basal levels of serum LH were lower in EB-treated males and females. However, a robust response to KISS-10 was observed in Control and EB-treated males and females (FIG. 6). This finding suggests that the EB300 implant does not alter the development and functionality of either GnRH neurons or pituitary gonadotrophs, indicating the specificity of the biological impact of EB300.

Impact of EB300 on the Gonads

To determine if neonatal estradiol exposure impacted gonadal development in males, testes were collected at PND 1, 3, and 10, and the seminiferous tubule, rete testis, and testicular interstitium were stained with H&E and microscopically examined. No obvious histopathological difference was detected between Control and EB rats (FIG. 7A). However, when TUNEL staining, which detects cells that undergo programmed cell death, was performed, a number of germ cells from the EB300 group showed positive signals at the ages of PND 3 and 10 (FIG. 7B), indicating that the EB300 implant induces germ cell death in the testis. This finding was supported by decreased DDX4 (germ cell marker) staining in the same tissues (FIG. 7C). In females, however, TUNEL staining in the ovaries, oviducts, or uteri did not find any significant difference between the Control and EB300 groups (FIG. 8B). At PND 10, however, in the ovaries of EB300 rats, a number of germ cells were clustered together without undergoing germ cell cyst breakdown. Subsequent immunostaining for DDX4 and FOXL2 (granulosa cell marker) confirmed this phenomenon in the EB300 group when the oocytes of the Control group were separated as singular primordial follicles (FIG. 8C). This result is consistent with the previous report that E2 inhibits germ cell nest breakdown in the neonatal ovary (PMID: 17446182). Together, these results show that an EB300 implant may directly impact gonadal development.

Single Implant of EB300 in Prepubertal Rats Induces Complete Sterility in Males and Females

Fertility

To determine if the impact on the Kisspeptin neurons and the gonads induces sterility, proven breeders were introduced to the cages of the Control and EB300 rats, kept with them for two weeks, and counted the numbers of litters and pups born to them. The Control rats produced litters, the EB-treated rats produced no pups (Table 1).

TABLE 1

| | Fertility (Male and Females) | | | |
|---|---|---|---|---|
| | Males | | Females | |
| Treatment | Control (n = 3) | EB300 (n = 3) | Control (n = 14) | EB300 (n = 7) |
| Age (months) | 4 | 4 | 3 | 3 |
| Fertility | 3/3 | 0/3 | 12/14 | 0/7 |
| Fertility (%) | 100 | 0 | 85.7 | 0 |
| Pups/litter | 15 | 0 | 12 | 0 |

Impact on Female Reproductive Organs

Figure 10:
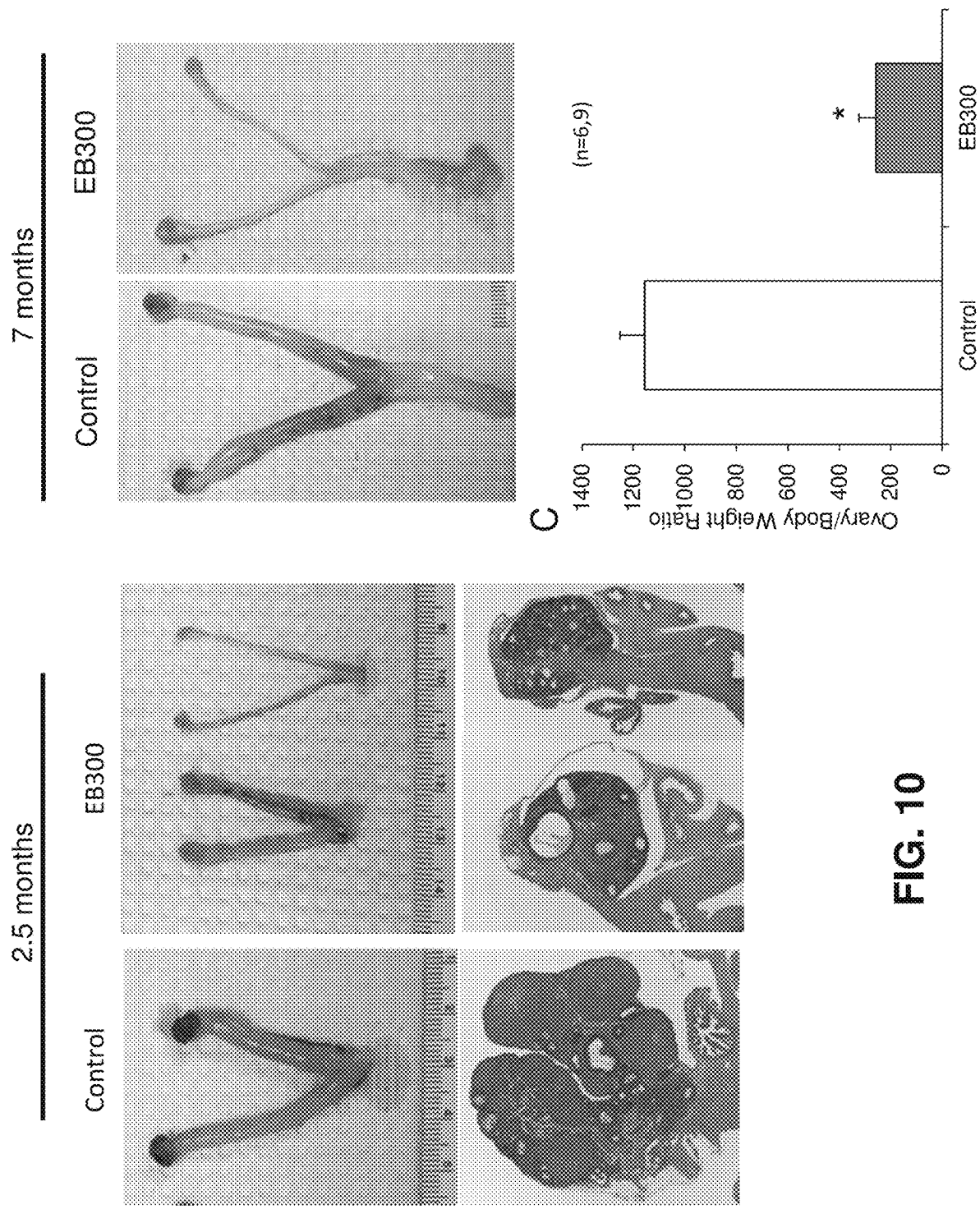
FIG. 10 depicts ovary, uterus, and pituitary at 2.5 and 7 months. Images were taken immediately after tissue collection or after H&E staining. The graph is from seven-month-old rats.

In females, EB300-implanted/treated animals did not exhibit any sign of estrus cyclicity as determined by vaginal cytology, and their vaginal openings remained narrow and obstructed (Table 2). Morphological and histological examination of 5.5-month old rats' ovaries and the uteri of the EB300 group were smaller and thinner, respectively, than those of the Control group (FIGS. 9 and 10). EB300-treated rats were deficient of glands in the uterus and corpus luteum in the ovary (FIGS. 9 and 10). The ovaries and uteri of younger (2.5 months) and older (seven months) EB300-treated rats showed similar morphological and histological patterns (FIG. 10), indicating that these phenotypes persist. However, in the pituitary, no substantial differences were seen (FIG. 5), suggesting an organ-specific effect of the EB300 implant.

TABLE 2

| | Estrous cycling Pattern | |
|---|---|---|
| Treatment | Control (n = 6) | EB300 (n = 24) |
| Age (months) | 2 | 2 |
| Estrous cycle (% normal pattern) | 100 (6/6) | 0 (0/24) |

Impact on Male Reproductive Organs

Figure 11:
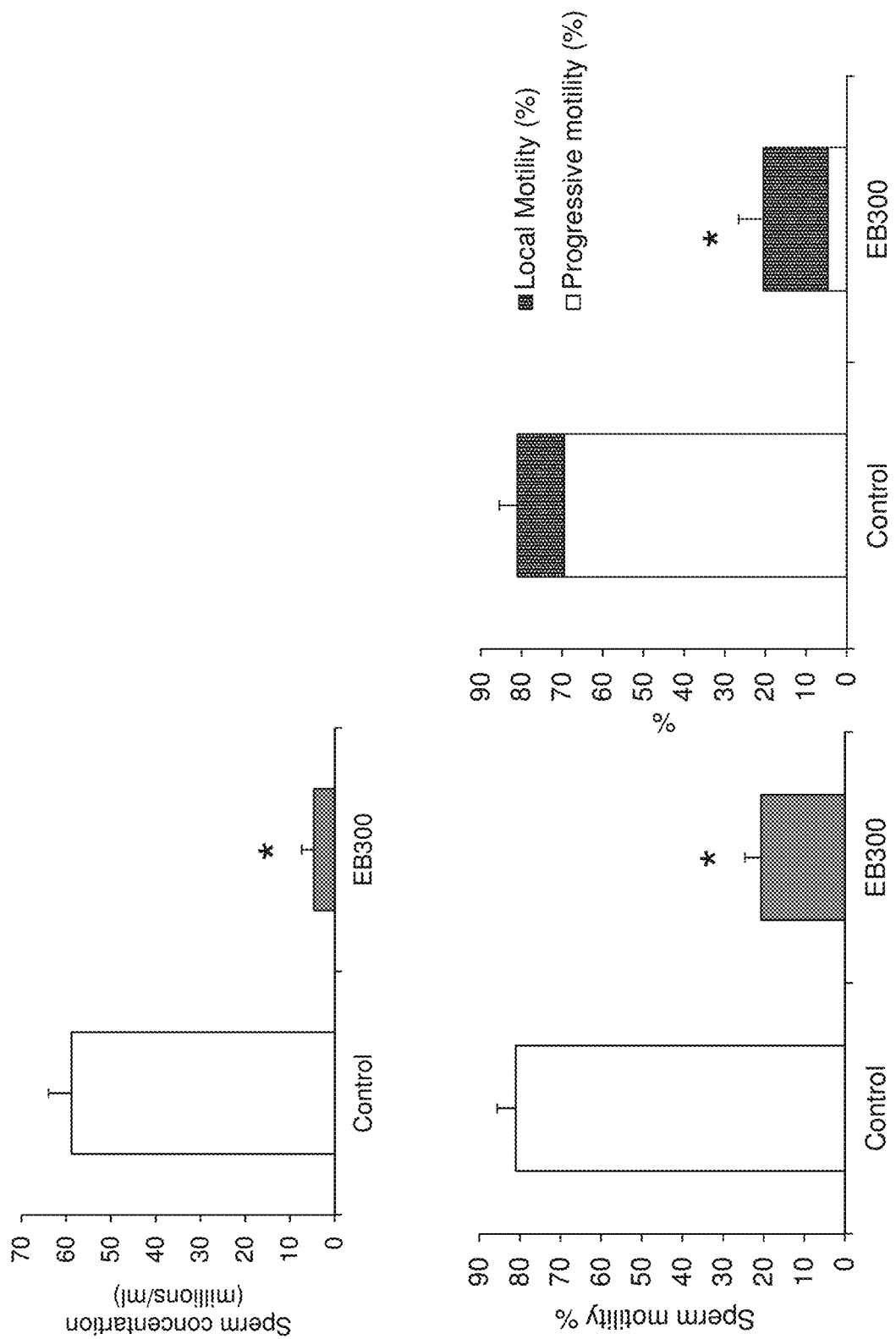
FIG. 11 shows sperm counts and motility (five to six months). Sperm concentrations and motility were measured by CASA at five to six months of ages. Four animals were used for the Control group and three for the EB300 group. Data are mean±SEM, * indicates p<0.05 when compared with the control group.

To determine if sperm counts and motility were affected by the neonatal EB300 implant, sperm numbers and quality were measured at five months of age. Sperm concentration (millions/mL) was significantly lower in the EB-treated group (p=0.001) compared to the Control group (FIG. 11). The motile sperm percentage was significantly decreased in the EB300-implanted rats (p=0.003). In addition, the percentage of progressive motile sperm was significantly decreased in the EB300-treated rats (p=0.02), and it had a significantly higher percentage of immotile sperm (p=0.01) compared to the Control rats (FIG. 11). These results indicate that the neonatal EB300 implant affects sperm concentration and quality, impacting male fertility.

Figure 12A:
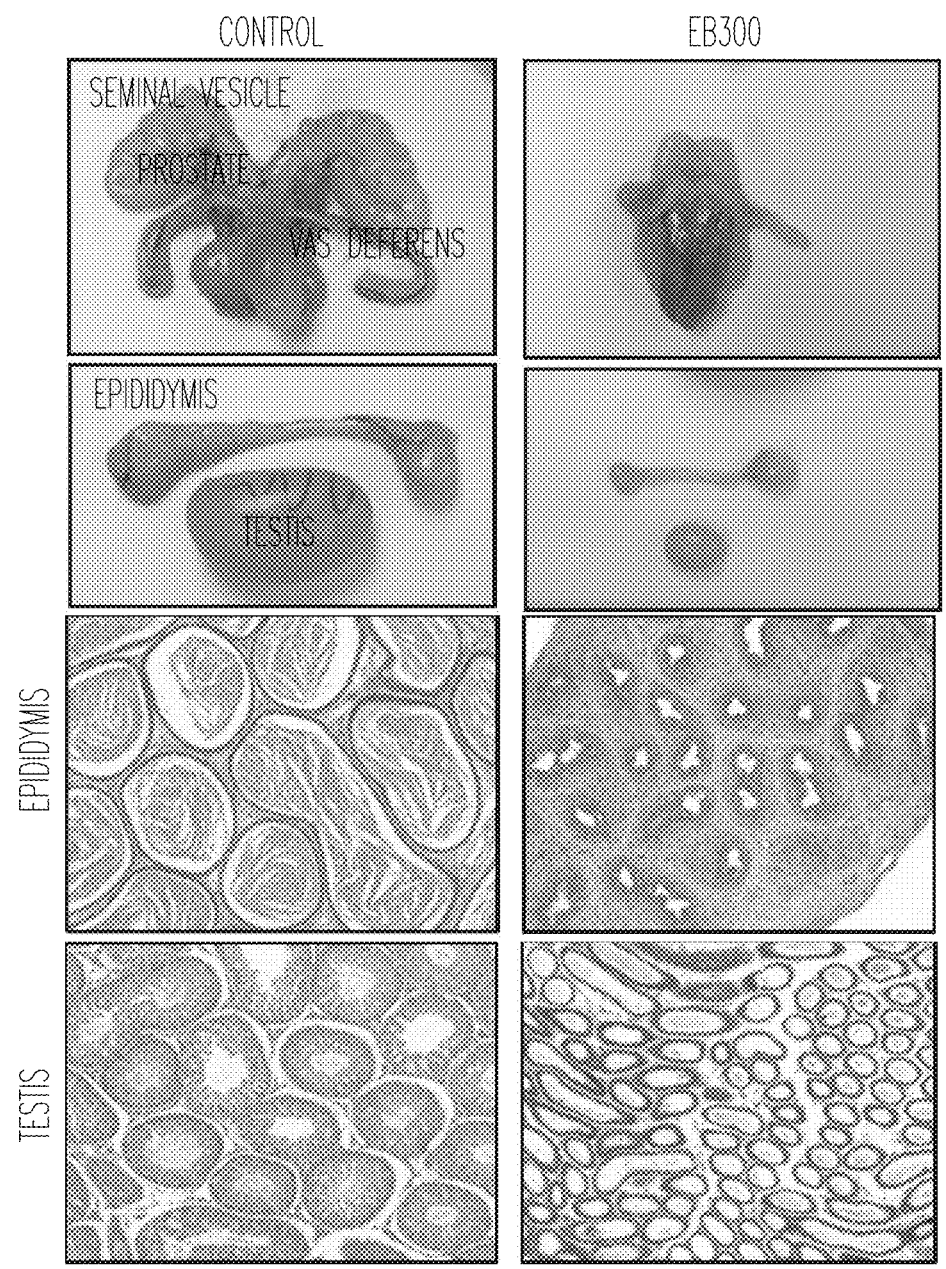
FIGS. 12A-B depict male gonads, epididymis, and accessory glands. Gonads, epididymis, and accessory glands were collected at the age of 2.5 months, and their morphology and histology were examined (A) followed by immunohistochemistry with antibodies for StAR (Steroidogenic Acute Regulatory Protein) and DDX4 (B). Arrowheads indicate Leydig cells. White arrows indicate germ cells. Black arrows indicate apoptotic germ cells by TUNEL staining (which allows one to identify dying cells). Shown are representative images of tissues from four animals from each group.
Figure 12B:
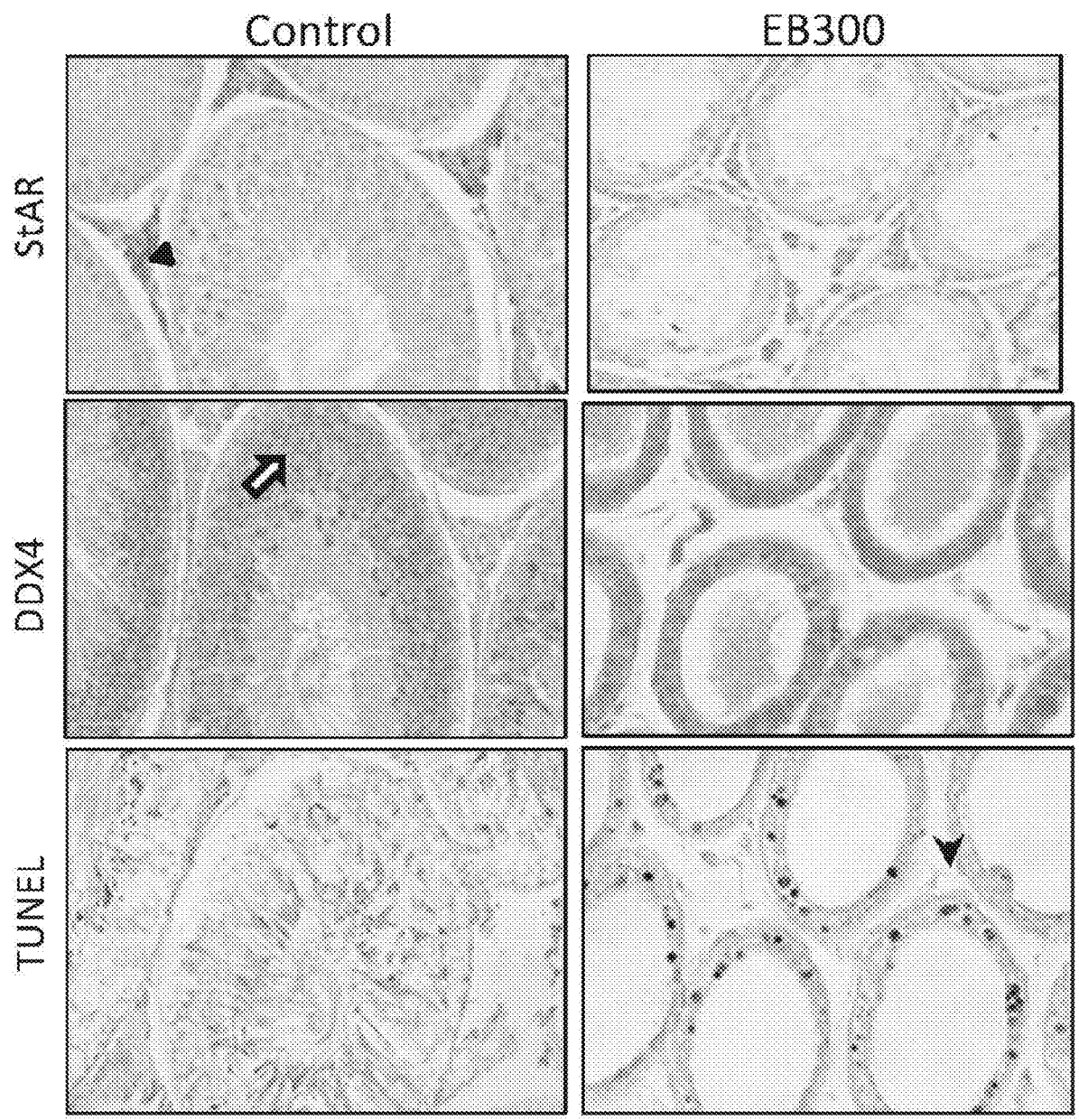
Figure 13:
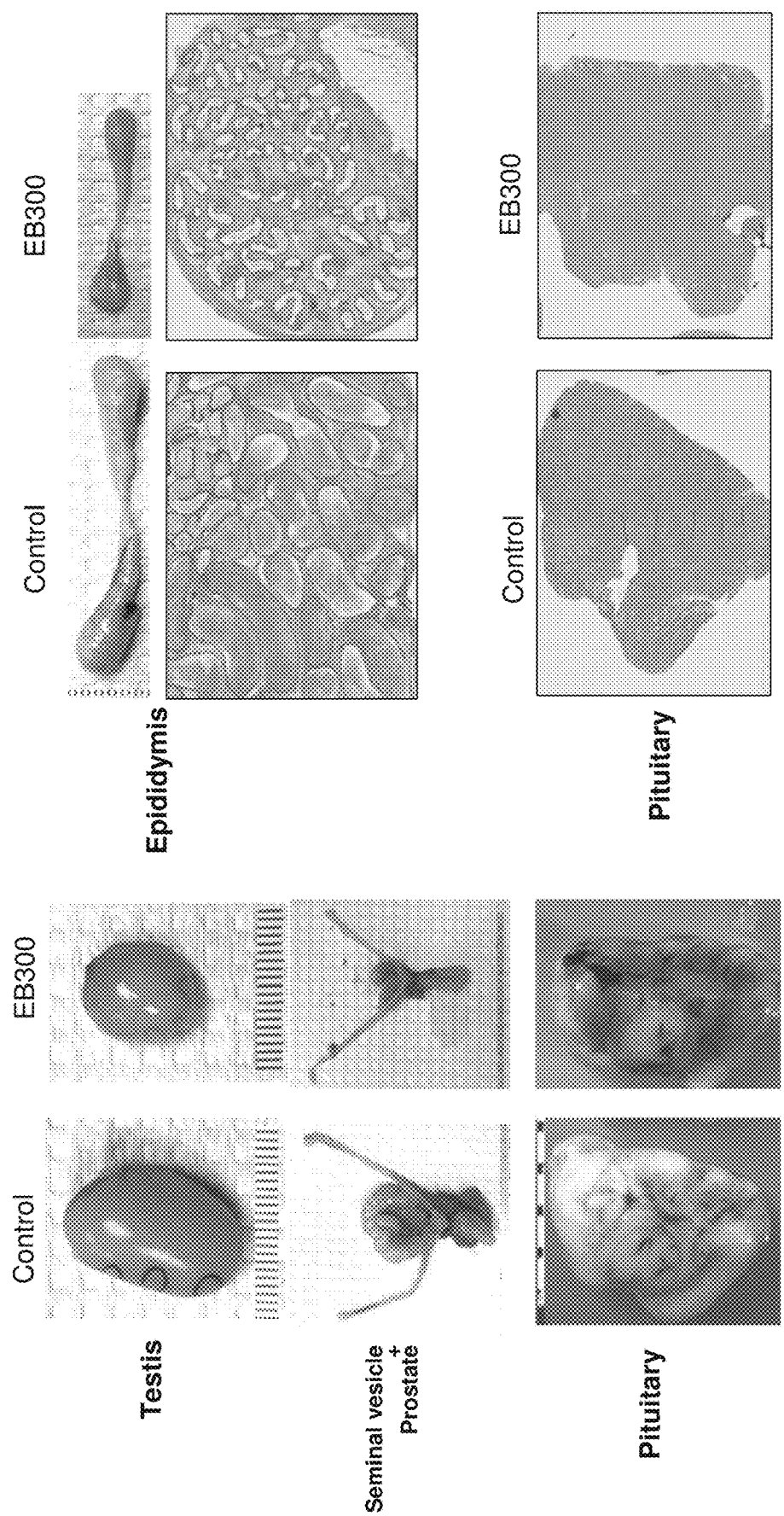
FIG. 13 depicts male gonads, epididymis, and accessory glands collected at the ages of 5-6 months.
Figure 14:
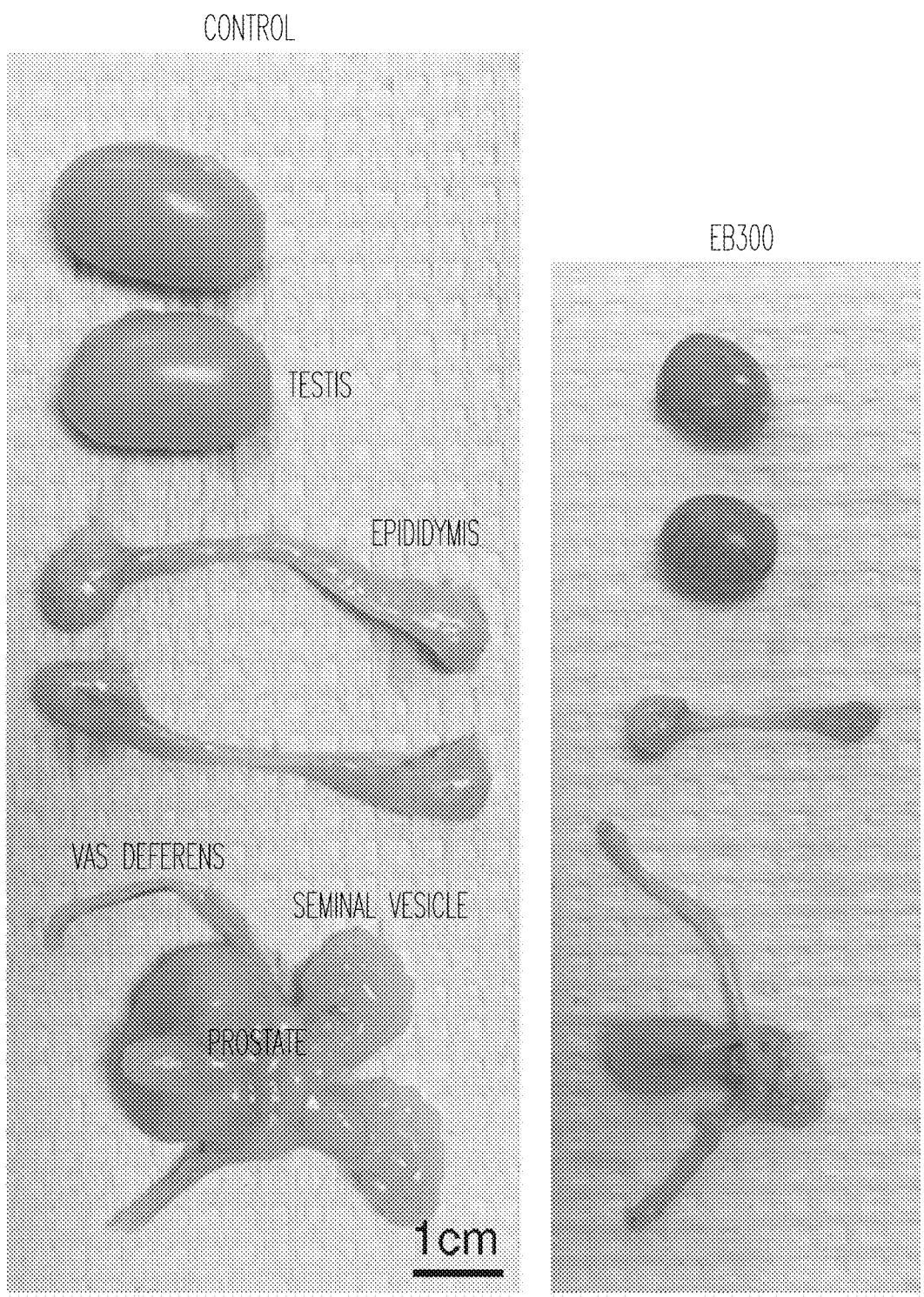
FIG. 14 depicts male gonads, epididymis and accessory glands collected at the ages of 6-7 months.
Figure 15:
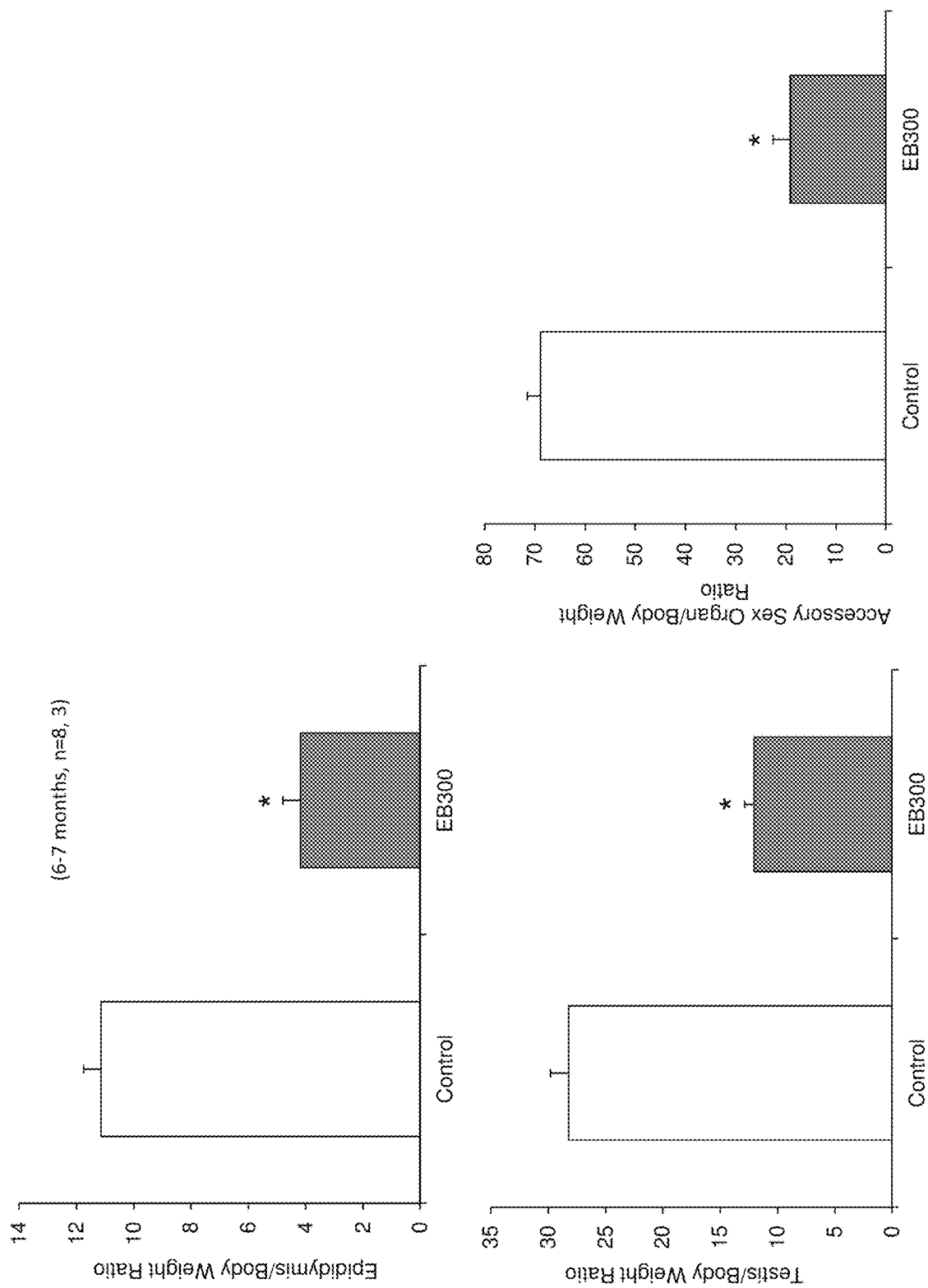
FIG. 15 shows bar graphs depicting of length of epididymis, testis weight, and accessory sex organ/body weight ratios (6-7 months; n=8, 3).

When examined at the age of 2.5 months, both the EB300 group of animals had significantly smaller testis, epididymis, seminal vesicles, and prostate glands compared the Control group (FIG. 12A). Epididymis from EBx11 and EB300 groups had smaller tubule diameters and contained few or no germ cells (FIG. 12A). Lower StAR (a marker for steroidogenic cell; Leydig cell) and DDX4 (germ cell marker) expression and a higher number of TUNEL positive cells in the EB300 animals suggest the EB300 implant caused a lower testosterone synthetic capacity, lower sperm production, and a higher level of apoptosis (FIG. 12B). Similar impacts on the testes and epididymis were strikingly evident in older animals (FIGS. 13 and 14). No significant difference in pituitary glands was observed between the Control and EB animals (FIGS. 13 and 14). When tissue weights were compared, the testis, epididymis, and accessory glands were lighter in the EB300 groups than in the Control groups (FIG. 15).

Figure 16:
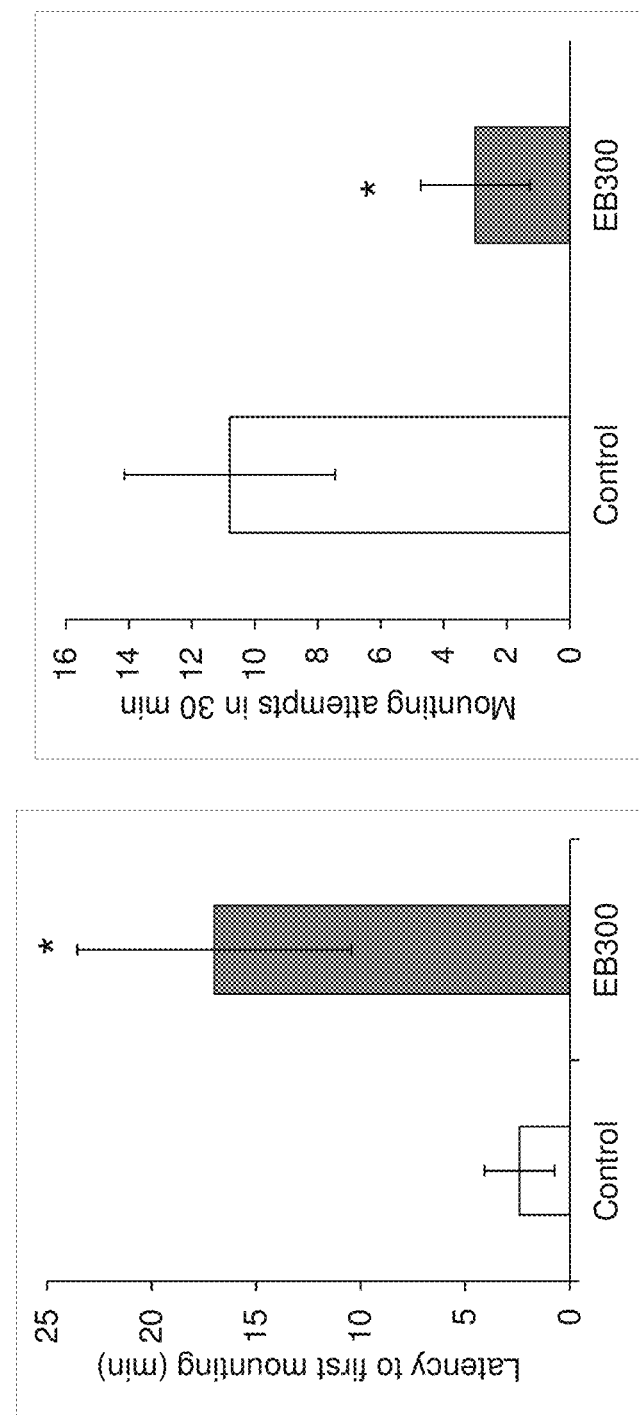
FIG. 16 shows bar graphs depicting mating behavior displayed by males. Male rats at four months of age were allowed to mount ovariectomized females, and the sexual behavior was measured during a 30-minute time period. (A) Latency to first mount during the experimental time (seconds). (B) Total numbers of mounting by males during the experimental time. Number of rats, Control group=5, EB300 group=3. Graphs show mean±SEM, * indicates p<0.05 when compared with the control group.

Male sexual behavior is dependent mainly on testosterone, the hormone that is secreted by the Leydig cells of the testes in all vertebrate species. To assess the sexual behavior of EB-treated rats, four-month-old males were housed with females that were at estrus, a reproductive stage when females are receptive to males, allowing the males to mount. The time taken to the first mount (latency) and the number of mounts in 30 minutes were recorded and compared. The EB300-treated animals had significantly longer latency (p=0.01) and made fewer mounting attempts (p=0.02) compared to the Control animals (FIG. 16), indicating that the EB implant significantly decreased mating behaviors in males.

Taken together, these reproductive traits show that neonatal implant of the EB capsule significantly inhibits gonadal and accessory gland development, gametogenesis, and sexual behavior, causing both males and females to be sterile.

Figure 17:
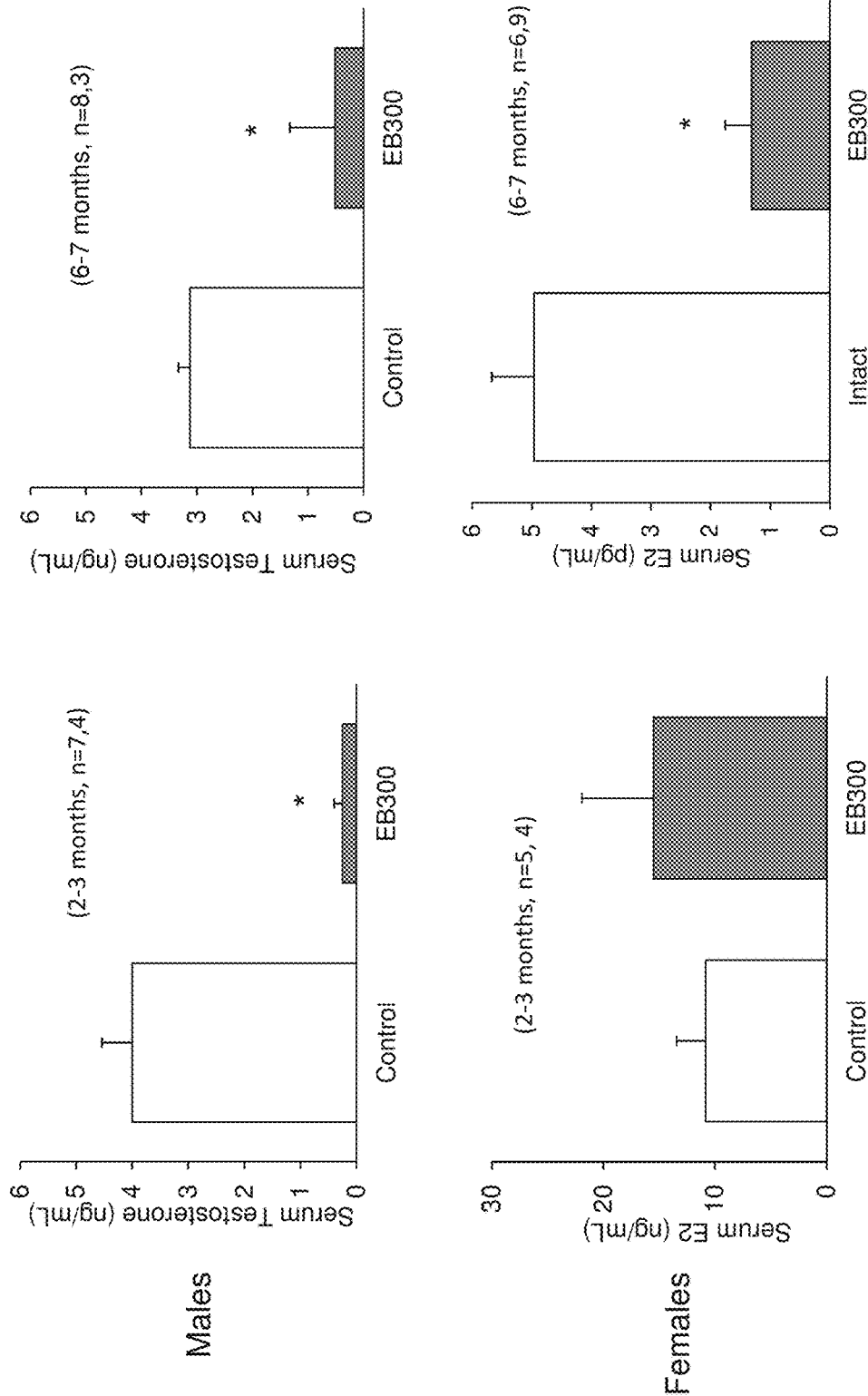
FIG. 17 shows bar graphs depicting serum T and E2 levels in young adult and mature animals. Serum testosterone concentrations were measured at the ages of 2-3 and 6-7 months in males. Serum estradiol concentrations were measured at the ages of two months and six months in females. Note the differences in the Y scales of serum estradiol levels in females. Shown are mean±SEM; * indicates p<0.05 when compared with the control group. Serum estradiol concentrations were measured at two and six months of age.
Figure 18:
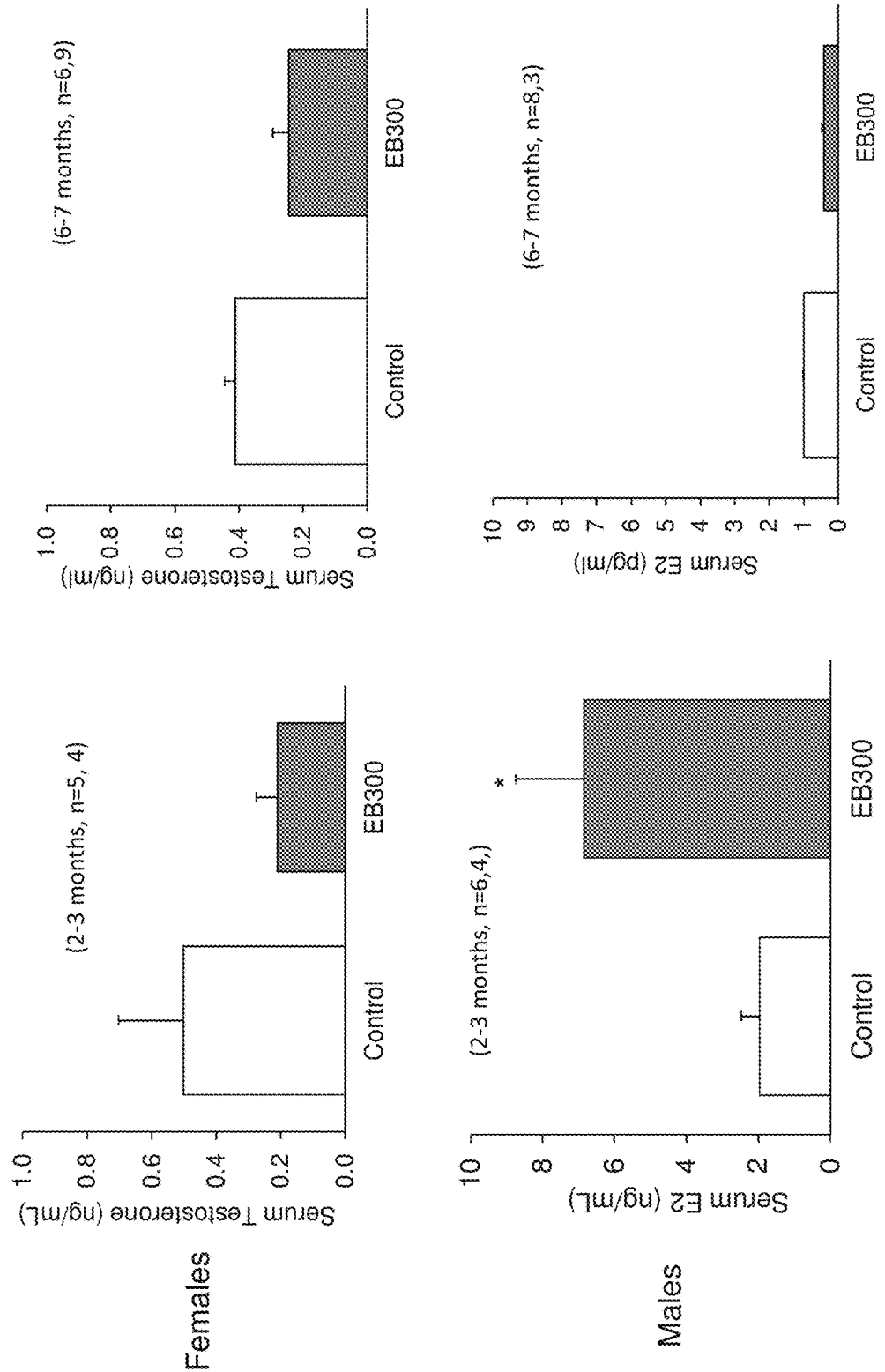
FIG. 18 shows bar graphs depicting serum T and E2 levels in young adult animals. Serum testosterone concentrations were measured at the ages of 2-3 and 6-7 months in females.

Rats Implanted with an Estradiol Benzoate-Containing Silicone Capsule (EB) Produce Significantly Less Gonadal Sex Steroids than Controls in Both Males and Females Defective development of the reproductive system will inevitably impact sex steroid hormone synthesis, so blood concentrations of sex steroids were examined. Peripheral blood was collected from males at two and six months of age and their serum hormone levels measured. At 2-3 months of age, serum testosterone levels of the EB300-treated group were significantly lower than those of the Control group (FIG. 17). The same trend was also seen when the testosterone concentrations were measured at 6-7 months of age (FIG. 17). In females, serum E2 levels were not significantly different among the EB300-treated and Control groups when they were young. However, E2 levels in the EB300-treated group of animals were significantly lower than those of the Control group (FIG. 17). On the other hand, testosterone levels in females were not different among the EB300-treated and the Control groups regardless of their ages. Interestingly, males implanted with an EB300 capsule had a significantly higher E2 concentration compared to the male Control group (FIG. 18), which may be due to increased aromatase activity in the male gonad. On the other hand, the low testosterone levels in males and low E2 levels in the adult females of EB-treated animals were expected due to the defective testis development and ovary development, respectively (FIGS. 7-14). The defective development of seminal vesicles and prostates and low mating behavior in the EB-treated animals may be due to these low testosterone levels, as their development depends on testosterone.

Animals with EB300 Implant do not Display Pathology

Figure 19:
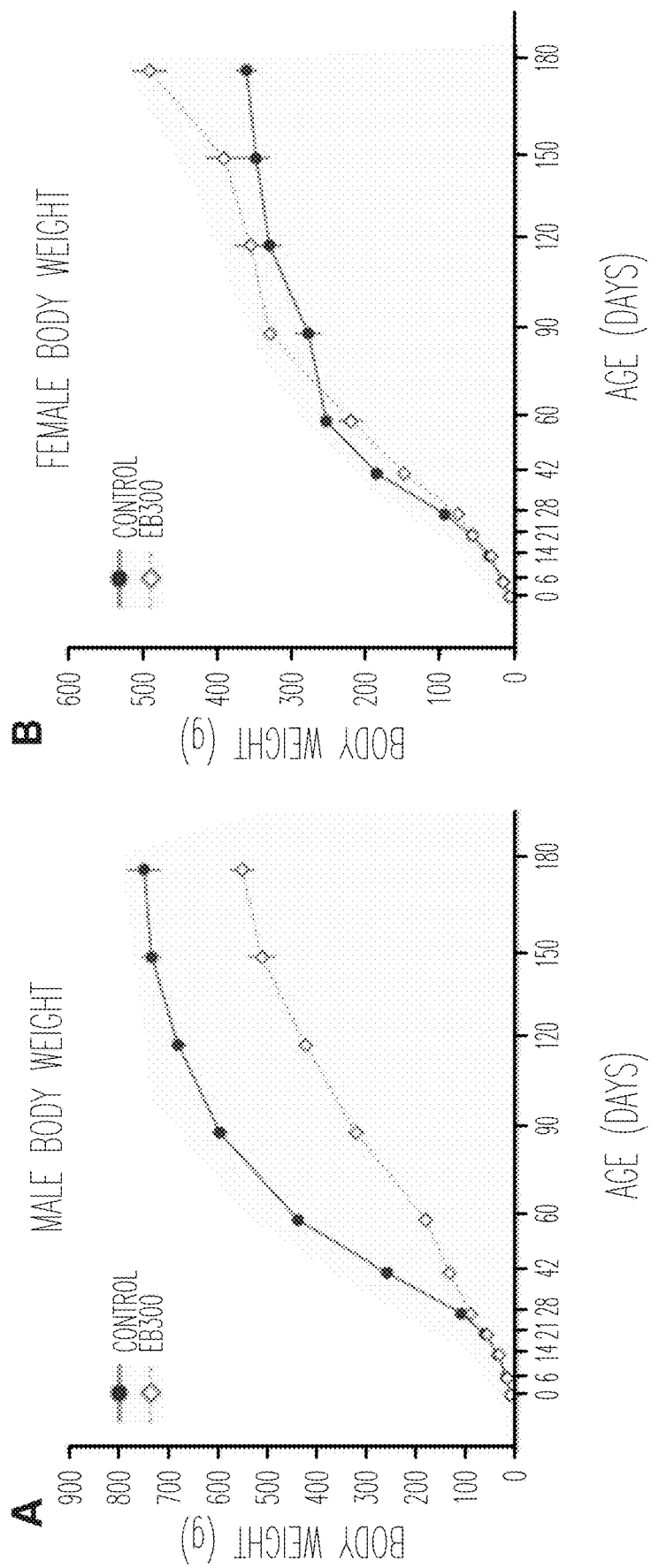

Body weight is often measured as a proxy for health status. EB300-treated and Control animals were weighed from birth until 180 days of age (FIG. 19). In males, the body weight of the EBx11 and EB300-treated groups was lower than the body weight in the Control group. At 180 days of age, the body weight of the EB300-treated group was significantly lower than that of the body weight in the Control group, but not significantly different among the other experimental groups (FIG. 19A). In females, EB-treated rats gained body weight more rapidly than the Control group rats. At 180 days of age, all EB-treated groups showed significantly higher body weight than the Control group (FIG. 19B).

When the rats reached the ages of 6-7 months, they were euthanized, and the ratios of organ length/body weight or organ weight/body weight were compared. Femur bone length/body weight did not differ between the Control and the EB300 group in males (FIG. 20). The brain/body weight and pituitary/body weight ratios of the EB300 group were higher, and the kidney/body weight ratio of the EB300 group was lower, than that of the Control group. The weight of the liver, spleen, and heart remained substantially the same between the Control and EB300 groups in males (FIG. 20). In females, the EB300 group showed decreased organ/body weight ratios in all organs of the EB300 group (FIG. 21). However, these differences may be due to the impact on body weight growth; the EB300 females were significantly heavier (approximately 20%) than the Controls (FIG. 21). In support, histological examination of kidney and liver found no pathology in any of the groups (FIG. 22). Blood chemistry also revealed no pathology in the kidney and liver (Data not shown). Carnoy's staining on whole-mount mammary glands revealed normal branching of the mammary glands in the EB300 groups. However, shrinkage/under-development of terminal end buds were apparent in the EB300 group. The low budding is thought to be caused by low E2 levels in the EB300 group (FIG. 23).

To investigate the effect of EB injection on hematopoiesis, blood cells, red blood cells (RBC), hemoglobin, platelets, and hemoglobin amount per red blood cell (MCH), mean corpuscular hemoglobin concentration (MCHC), and white blood cell (WBC) were counted (Table 3). In both males and females, RBC, platelet, and WBC counts were not different from those of the Controls, nor were there differences in the concentrations of hemoglobin, MCH, and MCHC. Taken together, the overall histology and hematology data indicate that hematopoiesis is not impacted by the EB implant.

TABLE 3

Hemato-biochemistry (5-7 months)

| Criteria | Male | | | | | | | |
|---|---|---|---|---|---|---|---|---|
| | Control (n = 10) | | EBx11 (n = 10) | | EB300 (n = 2) | | EB30 (n = 1) | |
| Red Blood Cells (x10^6/ul) | 8.58 | ±0.12 | 8.55 | ±N/A | 7.64 | 0.19 | 8.16 | ±N/A |
| Hemoglobin (g/dL) | 14.55 | ±0.28 | 16.20 | ±N/A | 14.00 | ±0.40 | 14.10 | ±N/A |
| Platelets (x10^3/ul) | 1313.10 | ±75.13 | 895.00 | ±N/A | 955.50 | ±183.50 | 1207.00 | ±N/A |
| MCH (pg) | 16.97 | ±0.24 | 18.90 | ±N/A | 18.35 | ±0.05 | 17.30 | ±N/A |

TABLE 3-continued

| | Hemato-biochemistry (5-7 months) | | | | | | | |
|---|---|---|---|---|---|---|---|---|
| MCHC (g/dL) | 32.46 | ±0.21 | 32.50 | ±N/A | 32.05 | ±0.15 | 32.50 | ±N/A |
| White Blood Cell Count (x10^3/ul) | 0.21 | ±0.98 | 8.71 | ±N/A | 10.30 | ±0 | 9.21 | ±N/A |

| | Female | | | | | | | |
|---|---|---|---|---|---|---|---|---|
| Criteria | Control (n = 12) | | EBx11 (n = 4) | | EB300 (n = 5) | | EB30 (n = 2) | |
| Red Blood Cells (x10^6/ul) | 7.63 | ±0.14 | 8.12 | ±0.21 | 7.58 | ±0.29 | 7.31 | ±0.14 |
| Hemoglobin (g/dL) | 13.98 | ±0.29 | 15.18 | ±0.34* | 14.28 | ±0.50 | 13.45 | ±0.05 |
| Platelets (x10^3/ul) | 854.08 | ±26.33 | 737.50 | ±28.68* | 884.20 | ±22.51 | 1079.00 | ±29.00* |
| MCH (pg) | 18.29 | ±0.20 | 18.70 | ±0.08 | 18.88 | ±0.21 | 18.35 | ±0.25 |
| MCHC (g/dL) | 32.34 | ±0.14 | 32.08 | ±0.30 | 32.02 | ±0.07 | 31.65 | ±0.25 |
| White Blood Cell Count (x10^3/ul) | 7.99 | ±0.81 | 9.01 | ±1.06 | 10.87 | ±1.38 | 8.45 | ±1.65 |

Data was presented by average ± SEM
*significantly different from control group (Student's t-test, $p < 0.05$)

EB300 has a Wider Effective Temporal Window

Knowing that implanting EB300 on PND 1 induced complete and irreversible infertility, it was then tested if infertility could be induced when the capsule was implanted at a later time point. The EB300 was implanted on PND 1, 5, 12 and 21. Surprisingly, all of the implantations at these different times effectively inhibited gonadal development in males as determined by the sizes of the testis and testicular histology accompanied by immunohistochemistry using antibodies for Cyp17 (Leydig cell marker), DDX4, and TUNEL staining (FIG. 24). The seminal vesicles and prostates were also markedly smaller (FIG. 25). In females, ovaries were smaller and no corpus luteum was found, indicating absence of ovulation (FIG. 26). Taken together, EB300 has a wide temporal window of effectiveness in inducing sterility both in males and females.

EB100 and EB30 are Also Effective in Inducing Sterility

The data presented below demonstrate that EB30 (30 μg of EB) was effective in sterilizing male and female animals (rat; implanted with EB on PND1 or 2).

| | Males | | Females | |
|---|---|---|---|---|
| Treatment | Control (n = 3) | EB30 (n = 3) | Control (n = 14) | EB30 (n = 4) |
| Age (months) | 3-6 | 3-6 | 3-6 | 3-6 |
| Fertility | 3/3 | 0/3 | 12/14 | 0/4 |
| Fertility (%) | 100 | 0 | 85.7 | 0 |
| Pups/litter | 15 | 0 | 12 | 0 |

EB is Effective in Inducing Sterility in Hamsters

The impact of an EB125 implant on gonadal development in hamsters was determined. Twenty-one-day-old hamsters were implanted with either an empty capsule (control) or 125 micrograms of EB contained in a silastic capsule. Reproductive tissues were collected from the subjects at PND30. Testes from hamsters implanted with EB125 were substantially smaller than those of the control animals.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof) or with respect to other examples (or one or more aspects thereof) shown or described herein.

In the event of inconsistent usages between this document and any documents so incorporated by reference, the usage in this document controls.

The above description is intended to be illustrative and not restrictive. For example, the above-described examples (or one or more aspects thereof) may be used in combination with each other. Other embodiments can be used, such as "by one of ordinary skill in the art" upon reviewing the above description. The Abstract is provided to comply with 37 C.F.R. § 1.72(b) to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in fewer than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims along with the full scope of equivalents to which such claims are entitled.

What is claimed is:

1. A method for inducing permanent sterility in an animal comprising subcutaneously administering to said animal an effective amount of estradiol, estradiol benzoate, estradiol dipropionate, estradiol valerate, estradiol cypionate or a combination thereof so as to render the animal permanently sterile,
  wherein said effective amount of estradiol, estradiol benzoate, estradiol dipropionate, estradiol valerate, estradiol cypionate, or a combination thereof is 1 mg/kg up to about 100 mg/kg,
  wherein the estradiol, estradiol benzoate, estradiol dipropionate, estradiol valerate, estradiol cypionate, or a combination thereof is formulated in a slow release formulation, wherein the sustained release formulation comprises a polymer, wherein the estradiol, estradiol benzoate, estradiol dipropionate, estradiol valerate, estradiol cypionate, or a combination thereof is released over a period of weeks, wherein the animal is a dog or cat, wherein the estradiol, estradiol benzoate, estradiol dipropionate, estradiol valerate, estradiol cypionate, or a combination thereof is administered to the cat or dog prior to puberty.

2. The method of claim 1, wherein the estradiol benzoate, estradiol dipropionate, estradiol valerate, estradiol cypionate, or a combination thereof is administered in a composition comprising a carrier.

3. The method of claim 2, wherein the carrier is a physiologically acceptable oil.

4. The method of claim 1, wherein the administration is a single dose, one time, administration.

5. A method for inducing permanent sterility in an animal comprising administering to said animal an effective amount of estradiol, estradiol benzoate, estradiol dipropionate, estradiol valerate, estradiol cypionate or a combination thereof so as to render the animal permanently sterile, wherein the estradiol, estradiol benzoate, estradiol dipropionate, estradiol valerate, estradiol cypionate, or a combination thereof is administered subcutaneously, wherein said effective amount of estradiol, estradiol benzoate, estradiol dipropionate, estradiol valerate, estradiol cypionate, or a combination thereof is 1 mg/kg up to about 100 mg/kg, wherein the estradiol, estradiol benzoate, estradiol dipropionate, estradiol valerate, estradiol cypionate, or a combination thereof is formulated in a slow release formulation, wherein the sustained release formulation comprises a polymer, wherein the estradiol, estradiol benzoate, estradiol dipropionate, estradiol valerate, estradiol cypionate, or a combination thereof is released over a period of weeks, wherein the animal is a female dog or female cat, wherein the estradiol, estradiol benzoate, estradiol dipropionate, estradiol valerate, estradiol cypionate, or a combination thereof is administered to the cat or dog prior to puberty.

6. The method of claim 1, wherein the estradiol, estradiol benzoate, estradiol dipropionate, estradiol valerate, estradiol cypionate, or a combination thereof is administered subcutaneously weeks, months or years after birth, but prior to the animal reaching puberty.

7. The method of claim 1, wherein the administration of the estradiol, estradiol benzoate, estradiol dipropionate, estradiol valerate, estradiol cypionate, or a combination thereof prevents reproductive organs from functioning.

8. The method of claim 5, wherein the administration of the estradiol, estradiol benzoate, estradiol dipropionate, estradiol valerate, estradiol cypionate, or a combination thereof blocks maturation of sex organs/gonads.

9. The method of claim 1, wherein the estradiol, estradiol benzoate, estradiol dipropionate, estradiol valerate, estradiol cypionate, or a combination thereof is released over 15 to 20 days.

10. The method of claim 5, wherein the estradiol, estradiol benzoate, estradiol dipropionate, estradiol valerate, estradiol cypionate, or a combination thereof is released over 15 to 20 days.

11. The method of claim 1, wherein the polymer is silicone.

12. The method of claim 1, wherein the polymer is a porous polymeric microparticle.

* * * * *